(12) United States Patent
Gribble et al.

(10) Patent No.: US 6,566,373 B2
(45) Date of Patent: May 20, 2003

(54) PROTEASE INHIBITORS

(75) Inventors: Andrew D Gribble, Herts (GB); Ashley Edward Fenwick, Stortford (GB); Robert W Marquis, St. Davids, PA (US); Daniel F Veber, Ambler, PA (US); Jason Witherington, Sawbridgeworth (GB)

(73) Assignees: SmithKline Beecham Corporation, Philadelphia, PA (US); SmithKline Beecham p.l.c., Brentford (GB)

( * ) Notice: Subject to any disclaimer, the term of this patent is extended or adjusted under 35 U.S.C. 154(b) by 0 days.

(21) Appl. No.: 09/917,990

(22) Filed: Jul. 30, 2001

(65) Prior Publication Data
US 2002/0013360 A1 Jan. 31, 2002

Related U.S. Application Data

(63) Continuation of application No. 09/672,219, filed on Sep. 28, 2000, which is a continuation of application No. 09/423,377, filed as application No. PCT/US98/03200 on May 6, 1998, now abandoned.
(60) Provisional application No. 60/045,758, filed on May 6, 1997.

(51) Int. Cl.$^7$ .................. C07D 307/48; C07D 319/06; C07D 333/02; C12N 9/99; A01N 43/02
(52) U.S. Cl. .................. 514/314; 549/465; 549/55; 549/321; 549/293; 549/468; 546/172; 546/169; 546/284.7; 546/214; 548/465; 514/464; 514/443; 514/472; 514/459; 514/414; 514/336; 514/326; 514/469
(58) Field of Search .................. 549/465, 55, 321, 549/293, 468; 514/464, 443, 472, 459, 314, 414, 336, 326, 469; 546/172, 169, 284.7, 214; 548/465

(56) References Cited

FOREIGN PATENT DOCUMENTS

| GB | 2 282 598 | 12/1995 |
|---|---|---|
| WO | WO 97/16177 | 9/1997 |
| WO | WO 97/32846 | 12/1997 |
| WO | WO 98/04539 | * 2/1998 |
| WO | WO 98/05336 | * 2/1998 |
| WO | WO 98/04539 | 5/1998 |

OTHER PUBLICATIONS

Printout for Carret et al. J. Heterocycl. Chem.*
CAS Printout for Marquis et al., WO 98/05336.*
Carret et al. Route to a pyranic analogof puromycin, J. Heterocycl. Chem. 20: 687–703 (1983).*
Leung et al. Protease Inhibitors: Current Status and Future Prospects, J. Med. Chem. 43: 305–341 (2000).*
Printout for Carret, et al.; J. Heterocycl. Chem, Mar., 1983.
CAS Printout for Marquis, et al., (WO 98/05336), Mar., 1983.
Conroy, et al., J. AM. Chem. Soc., 1997, vol. 119, pp. 4285–4291.
Conroy, et al., Tetrahedron Letters, 1998, vol. 39, pp. 8253–8256.

* cited by examiner

*Primary Examiner*—Mukund J. Shah
*Assistant Examiner*—Hong Liu
(74) *Attorney, Agent, or Firm*—Laura K. Madden; Mary E. McCarthy; Charles M. Kinzig

(57) ABSTRACT

The invention relates to 3-hydroxy-and 3-keto-cyclohetero-substituted leucine compounds that are inhibitors of cysteine proteases, particularly cathepsin K, and are useful in the treatment of diseases in which inhibition of bone loss is a factor. The 3-hydroxy-or 3-keto-moiety is bonded to a tetrahydrothiophene, tetrahydrothiopyran, tetrahydrofuran or tetrahydropyran ring.

22 Claims, No Drawings

PROTEASE INHIBITORS

This is a continuation of application Ser. No. 09/672,219, filed Sep. 28, 2000, which is a continuation of application Ser. No. 09/423,377, filed Nov. 4, 1999, now abandoned, which is a 371 of International Application No. PCT/US98/03200, filed May 6, 1998, which claims priority to U.S. Provisional Application No: 60/045,758, filed May 6, 1997.

FIELD OF THE INVENTION

This invention relates to novel protease inhibitors, particularly inhibitors of cysteine and serine proteases, more particularly compounds which inhibit cysteine proteases. The compounds of this invention even more particularly relate to those compounds which inhibit cysteine proteases of the papain superfamily, and particularly cysteine proteases of the cathepsin family. In the most preferred embodiment, this invention relates to compounds which inhibit cathepsin K. Such compounds are particularly useful for treating diseases in which cysteine proteases are implicated, especially diseases of excessive bone or cartilage loss, e.g., osteoporosis, periodontitis, and arthritis.

BACKGROUND OF THE INVENTION

Cathepsin K is a member of the family of enzymes which are part of the papain superfamily of cysteine proteases. Cathepsins B, H, L, N and S have been described in the literature. Recently, cathepsin K polypeptide and the cDNA encoding such polypeptide were disclosed in U.S. Pat. No. 5,501,969 (called cathepsin O therein). Cathepsin K has been recently expressed, purified, and characterized. Bossard, M. J., et al., (1996) *J. Biol. Chem.* 271, 12517–12524; Drake, F. H., et al., (1996) *J. Biol. Chem.* 271, 12511–12516; Bromme, D., et al., (1996) *J. Biol. Chem.* 271, 2126–2132.

Cathepsin K has been variously denoted as cathepsin O, cathepsin X or cathepsin O2 in the literature. The designation cathepsin K is considered to be the more appropriate one (name assigned by Nomenclature Committee of the International Union of Biochemistry and Molecular Biology).

Cathepsins of the papain superfamily of cysteine proteases function in the normal physiological process of protein degradation in animals, including humans, e.g., in the degradation of connective tissue. However, elevated levels of these enzymes in the body can result in pathological conditions leading to disease. Thus, cathepsins have been implicated in various disease states, including but not limited to, infections by pneumocystis carinii, trypsanoma cruzi, trypsanoma brucei brucei, and Crithidia fusiculata; as well as in schistosomiasis malaria, tumor metastasis, metachromatic leukodystrophy, muscular dystrophy, amytrophy, and the like. See International Publication Number WO 94/04172, published on Mar. 3, 1994, and references cited therein. See also European Patent Application EP 0 603 873 A1, and references cited therein. Two bacterial cysteine proteases from *P. gingivallis*, called gingipains, have been implicated in the pathogenesis of gingivitis. Potempa, J., et al. (1994) *Perspectives in Drug Discovery and Design*, 2, 445–458.

Cathepsin K is believed to play a causative role in diseases of excessive bone or cartilage loss. Bone is composed of a protein matrix in which spindle- or plate-shaped crystals of hydroxyapatite are incorporated. Type I Collagen represents the major structural protein of bone comprising approximately 90% of the structural protein. The remaining 10% of matrix is composed of a number of non-collagenous proteins, including osteocalcin, proteoglycans, osteopontin, osteonectin, thrombospondin, fibronectin, and bone sialoprotein. Skeletal bone undergoes remodeling at discrete foci throughout life. These foci, or remodeling units, undergo a cycle consisting of a bone resorption phase followed by a phase of bone replacement.

Bone resorption is carried out by osteoclasts, which are multinuclear cells of hematopoietic lineage. The osteoclasts adhere to the bone surface and form a tight sealing zone, followed by extensive membrane ruffling on their apical (i.e., resorbing) surface. This creates an enclosed extracellular compartment on the bone surface that is acidified by proton pumps in the ruffled membrane, and into which the osteoclast secretes proteolytic enzymes. The low pH of the compartment dissolves hydroxyapatite crystals at the bone surface, while the proteolytic enzymes digest the protein matrix. In this way, a resorption lacuna, or pit, is formed. At the end of this phase of the cycle, osteoblasts lay down a new protein matrix that is subsequently mineralized. In several disease states, such as osteoporosis and Paget's disease, the normal balance between bone resorption and formation is disrupted, and there is a net loss of bone at each cycle. Ultimately, this leads to weakening of the bone and may result in increased fracture risk with minimal trauma.

The abundant selective expression of cathepsin K in osteoclasts strongly suggests that this enzyme is essential for bone resorption. Thus, selective inhibition of cathepsin K may provide an effective treatment for diseases of excessive bone loss, including, but not limited to, osteoporosis, gingival diseases such as gingivitis and periodontitis, Paget's disease, hypercalcemia of malignancy, and metabolic bone disease. Cathepsin K levels have also been demonstrated to be elevated in chondroclasts of osteoarthritic synovium. Thus, selective inhibition of cathepsin K may also be useful for treating diseases of excessive cartilage or matrix degradation, including, but not limited to, osteoarthritis and rheumatoid arthritis. Metastatic neoplastic cells also typically express high levels of proteolytic enzymes that degrade the surrounding matrix. Thus, selective inhibition of cathepsin K may also be useful for treating certain neoplastic diseases.

It now has been discovered that a novel class of compounds are protease inhibitors, most particularly inhibitors of cathepsin K, and these compounds are useful for treating diseases in which inhibition of bone resorption is indicated, such as osteoporosis and periodontal disease.

SUMMARY OF THE INVENTION

An object of the present invention is to provide protease inhibitors, such as inhibitors of cysteine and serine proteases. In particular, the present invention relates to compounds which inhibit cysteine proteases, and particularly cysteine proteases of the papain superfamily. Preferably, this invention relates to compounds which inhibit cysteine proteases of the cathepsin family and particularly, compounds which inhibit cathepsin K. The compounds of the present invention are useful for treating diseases, which may be therapeutically modified by altering the activity of such proteases.

Accordingly, in the first aspect, this invention provides a compound according to formula (I):

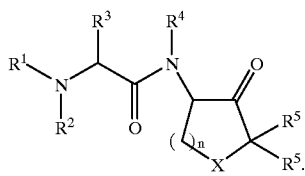

(I)

In another aspect, this invention provides a pharmaceutical composition comprising a compound according to formula (I) and a pharmaceutically acceptable carrier.

In yet another aspect, this invention provides a method of treating diseases in which the disease pathology may be therapeutically modified by inhibiting proteases, such as cysteine and serine proteases. In particular, the method includes treating diseases by inhibiting cysteine proteases, and particularly cysteine proteases of the papain superfamily. More particularly, the inhibition of cysteine proteases of the cathepsin family, such as cathepsin K is described.

In another aspect, the compounds of this invention are especially useful for treating diseases characterized by bone loss, such as osteoporosis and gingival diseases, such as gingivitis and periodontitis, or by excessive cartilage or matrix degradation, such as osteoarthritis and rheumatoid arthritis.

DETAILED DESCRIPTION OF THE INVENTION

The present invention provides compounds of formula (I):

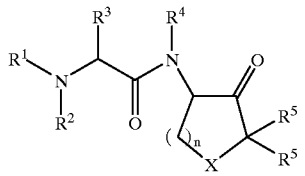

(I)

wherein:
$R^1$ is R", R"C(O), R"C(S), R"SO$_2$, R"OC(O), R"R'NC(O), or R"OC(O)NR'CH(R$^6$)C(O);
$R^2$ is H, $C_{1-6}$alkyl, $C_{2-6}$alkenyl, Ar-$C_{0-6}$alkyl, or Het-$C_{0-6}$alkyl;
$R^3$ is H, $C_{1-6}$alkyl, $C_{2-6}$alkenyl, $C_{2-6}$alkynyl, $C_{3-6}$cycloalkyl-$C_{0-6}$alkyl, Ar-$C_{0-6}$alkyl, or Het-$C_{0-6}$alkyl;
$R^4$ is H, $C_{1-6}$alkyl, $C_{2-6}$alkenyl, Ar-$C_{0-6}$alkyl, or Het-$C_{0-6}$alkyl;
each $R^5$ independently is H, $C_{1-6}$alkyl, $C_{2-6}$alkenyl, Ar-$C_{0-6}$alkyl, or Het-$C_{0-6}$alkyl;
$R^6$ is H, $C_{1-6}$alkyl, $C_{2-6}$alkenyl, $C_{3-6}$cycloalkyl-$C_{0-6}$alkyl, Ar-$C_{0-6}$alkyl, Het-$C_{0-6}$alkyl;
R' is H, $C_{1-6}$alkyl, $C_{2-6}$alkenyl, Ar-$C_{0-6}$alkyl, or Het-$C_{0-6}$alkyl;
R" is $C_{1-6}$alkyl, Ar-$C_{0-6}$alkyl, Het-$C_{0-6}$alkyl, Ar-$C_{2-6}$alkenyl or Het-$C_{2-6}$alkenyl;
X is O or S; and
n is 1, 2 or 3;
or a pharmaceutically acceptable salt thereof.

The present invention includes all hydrates, solvates, complexes and prodrugs of the compounds of this invention. Prodrugs are any covalently bonded compounds which release the active parent drug according to formula (I) in vivo. If a chiral center or another form of an isomeric center is present in a compound of the present invention, all forms of such isomer or isomers, including enantiomers and diastereomers, are intended to be covered herein. Inventive compounds containing a chiral center may be used as a racemic mixture, an enantiomerically enriched mixture, or the racemic mixture may be separated using well-known techniques and an individual enantiomer may be used alone. According to the instant invention, the S-form at the furan ring junction of formula (I) compounds is preferred.

In cases in which compounds have unsaturated carbon-carbon double bonds, both the cis (Z) and trans (E) isomers are within the scope of this invention. In cases wherein compounds may exist in tautomeric forms, such as keto-enol tautomers, each tautomeric form is contemplated as being included within this invention whether existing in equilibrium or predominantly in one form.

The meaning of any substituent at any one occurrence in formula (I) or any subformula thereof is independent of its meaning, or any other substituent's meaning, at any other occurrence, unless specified otherwise.
With respect to formula (I):
Suitably, $R^2$ and $R^4$ are H and $R^3$ is $C_{1-6}$alkyl or $C_{2-6}$alkenyl. Preferably, $R^3$ is i-butyl.
Suitably, each $R^5$ is H.
Suitably, $R^1$ is R"OC(O), R"SO$_2$ or R"C(O), in which R" is Ar-$C_{0-6}$alkyl or Het-$C_{0-6}$alkyl, and, most preferably, R" is

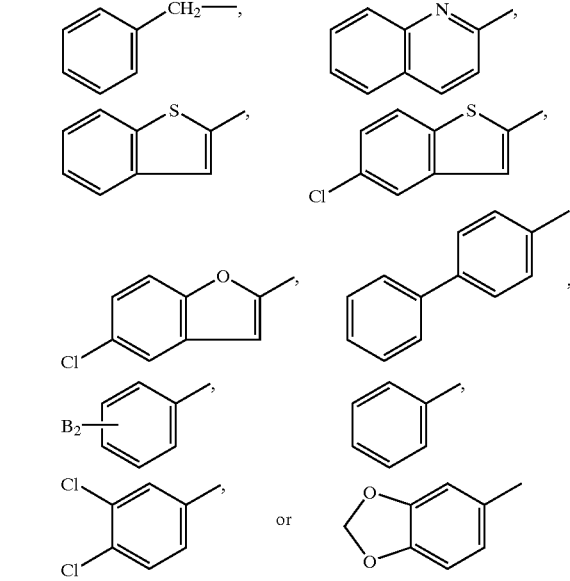

in which B$_2$ is OH, CN, OCF$_3$, OC$_{1-6}$alkyl, OAr, SO$_2$C$_{1-6}$alkyl, C$_{1-6}$alkyl or halo.
Suitably, n is 1 or 2. Preferably, n is 1.
Suitably, X is O.
In one particular embodiment, this invention is a compound of formula (II):

(II)

Preferably, the formula (I) compound of this invention is a compound of formula (IIa):

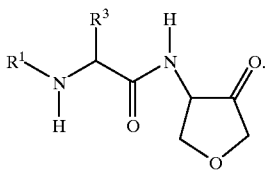

(IIa)

Alternately, the formula (I) compound of this invention is a compound of formula (IIb):

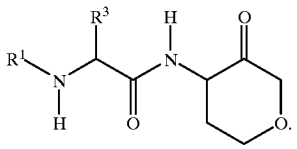

(IIb)

In another embodiment, this invention is a compound of formula (IIc):

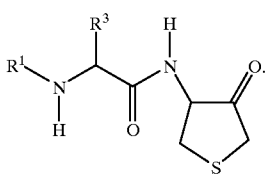

(IIc)

Specific representative compounds of this invention are:
4-(R,S)-Amino-N-[(3,4-methylenedioxybenzoyl)-S-leucine]-tetrahydrofuran-3-one;
4-(R,S)-Amino-N-[(benzyloxycarbonyl)-S-leucine]-tetrahydrofuran-3-one;
4-(R,S)-Amino-N-[(3,4-dichlorobenzoyl)-S-leucine]-tetrahydrofuran-3-one;
4-(R,S)-Amino-N-[(2-quinolinecarbonyl)-S-leucine]-tetrahydrofuran-3-one;
4-(R,S)-Amino-N-[(8-quinolinecarbonyl)-S-leucine]-tetrahydrofuran-3-one;
4-(R,S)-Amino-N-[(benzyloxycarbonyl)-S-leucine]-2,2-dibenzyl-tetrahydrofuran-3-one;
4-(R,S)-Amino-N[(benzo[b]thiophen-2-ylcarbonyl)-S-leucine]-tetrahydrofuran-3-one;
4-(R,S)-Amino-N-[(3,4-dimethoxybenzoyl)-S-leucine]-tetrahydrofuran-3-one;
4-(R,S)-Amino-N-[(indole-6-ylcarbonyl)-S-leucine]-tetrahydrofuran-3-one;
4-(R,S)-Amino-N-[(benzofuran-2-ylcarbonyl)-S-leucine)-tetrahydrofuran-3-one;
4-(R,S)-Amino-N-[(5-aminobenzo[b]thiophen-2-ylcarbonyl)-S-leucine]-tetrahydrofuran-3-one;
4-(R,S)-Amino-N-[(5-chlorobenzofuran-2-ylcarbonyl)-S-leucine]-tetrahydrofuran-3-one;
4-(R,S)-Amino-N-[(5-methoxybenzofuran-2-ylcarbonyl)-S-leucine]-tetrahydrofuran-3-one;
4-(R,S)-Amino-N-[(3-bromobenzoyl)-S-leucine]-tetrahydrofuran-3-one;
4-(R,S)-Amino-N-[(4-bromobenzoyl)-S-leucine]-tetrahydrofuran-3-one;
4-(R,S)-Amino-N-[(5-chlorobenzo[b]thiophen-2-ylcarbonyl)-S-leucine]-tetrahydrofuran-3-one;
4-(R,S)-Amino-N-[(4-fluorobenzo[b]thiophen-2-ylcarbonyl)-S-leucine]-tetrahydrofuran-3-one;
4-(R,S)-Amino-N-[(4-phenoxybenzoyl)-S-leucine]-tetrahydrofuran-3-one;
4-(R,S)-Amino-N-[(4phenylbenzoyl)-S-leucine]-tetrahydrofuran-3-one;
4-(R,S)-Amino-N-[(6-trifluoromethylbenzo[b]thiophen-2-ylcarbonyl)-S-leucine]-tetrahydrofuran-3-one;
4-(R,S)-Amino-N-[(4-ethyllbenzoyl)-S-leucine]-tetrahydrofuran-3-one;
4-(R,S)-Amino-N-[(4-(tert-butyl)benzoyl)-S-leucine]-tetrahydrofuran-3-one ;
4-(R,S)-Amino-N-[(5-methoxybenzo[b]thiophen-2-ylcarbonyl)-S-leucine]-tetrahydrofuran-3-one;
4-(R,S)-Amino-N-[(4-nitrobenzo[b]thiophen-2-ylcarbonyl)-S-leucine]-tetrahydrofuran-3-one;
4-(R,S)-Amino-N-[(6-bromobenzo[b]thiophen-2-ylcarbonyl)-S-leucine]-tetrahydrofuran-3-one;
4-(R,S)-Amino-N-[(5-bromobenzo[b]thiophen-2-ylcarbonyl)-S-leucine]-tetrahydrofuran-3-one;
4-(R,S)-Amino-N-[(6-methoxybenzo[b]thiophen-2-ylcarbonyl)-S-leucine]-tetrahydrofuran-3-one;
4-S-Amino-N-[(benzo(b)thiophen-2-ylcarbonyl)-S-leucine]-tetrahydrofuran-3-one;
4-R-Amino-N-[(benzo(b)thiophen-2-ylcarbonyl)-S-leucine]-tetrahydrofuran-3-one;
4-S-Amino-N-[(2-napthoyl)-S-leucine]-tetrahydrofuran-3-one;
4-R-Amino-N-[(2-napthoyl)-S-leucine]-tetrahydrofuran-3-one;
4-S-Amino-N-[(quinoline-2-carbonyl)-S-leucine]-tetrahydrofuran-3-one;
4-R-Amino-N-[(quinoline-2-carbonyl)-S-leucine]-tetrahydrofuran-3-one;
4-S-Amino-N-[(5-methoxybenzofuran-2-ylcarbonyl)-S-leucine]-tetrahydrofuran-3-one;
4-S-Amino-N-[((4-pyrid-3-yl)benzoyl)-S-leucine]-tetrahydrofuran-3-one;
4-S-Amino-N-[((4-pyrid-2-yl)benzoyl)-S-leucine]-tetrahydrofuran-3-one,
4-S-Amino-N-[(benzyloxycarbonyl)-S-leucine]-tetrahydrofuran-3-one;
4-S-Amino-N-[(3,4-dimethoxybenzoyl)-S-leucine]-tetrahydrofuran-3-one;
4-S-Amino-N-[(benzofuran-2-ylcarbonyl)-S-leucine]-tetrahydrofuran-3-one;
4-S-Amino-N-[(4-[6-methylpyrid-3-yl]benzoyl)-S-leucine]-tetrahydrofuran-3-one;
4-S-Amino-N-[(5-chlorobenzo[b]thiophen-2-ylcarbonyl)-S-leucine]-tetrahydrofuran-3-one;
4-S-Amino-N-[((4-pyrid4-yl)benzoyl)-S-leucine]-tetrahydrofuran-3-one;
4-S-Amino-N-[(2-chlorobenzoyl)-S-leucine]-tetrahydrofuran-3-one;
4-S-Amino-N-[(4-bromobenzoyl)-S-leucine]-tetrahydrofuran-3-one;
4-S-Amino-N-[(4-chlorobenzo[b]thiophen-2-ylcarbonyl)-S-leucine]-tetrahydrofuran-3-one;
4-S-Amino-N-[(4-benzylpiperidin-1-ylcarbonyl)-S-leucine]-tetrahydrofuran-3-one;
4-S-Amino-N-[(3,4-dichlorobenzoyl)-S-leucine]-tetrahydrofuran-3-one;
4-S-Amino-N-[(3-chlorobenzoyl)-S-leucine]-tetrahydrofuran-3-one;
4-(R,S)-Amino-N-[(3,4-dimethoxybenzoyl)-S-leucine]-tetrahydropyran-3-one;
4-(R,S)-Amino-N-[(4-phenoxybenzoyl)-S-leucine]-tetrahydropyran-3-one;
4-(R,S)-Amino-N-[(quinolin-2-ylcarbonyl)-S-leucine]-tetrahydropyran-3-one;

4-(R,S)-Amino-N-[(benzyloxycarbonyl)-S-leucine]-tetrahydropyran-3-one:

4-(R,S)-Amino-N-[(benzo[b]thiophen-2-ylcarbonyl)-S-leucine]-tetrahydropyran-3-one; and 4-(R,S)-Amino-N-[(benzo[b]thiophen-2-ylcarbonyl)-S-leucine]-tetrahydrothiophen-3-one;

or a pharmaceutically acceptable salt thereof.

In yet another aspect, this invention provides novel intermediates useful in the preparation of formula (I) compounds represented by formulae (III), (IV) and (V):

(III)

wherein:
R$^1$ is R", R"C(O), R"C(S), R"SO$_2$, R"OC(O), R"R'NC(O), or R"OC(O)NR'CH(R$^6$)C(O);

R$^2$ is H, C$_{1-6}$alkyl, C$_{2-6}$alkenyl, Ar-C$_{0-6}$alkyl, or Het-C$_{0-6}$alkyl;

R$^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;

R$^4$ is H, C$_{1-6}$alkyl, C$_{2-6}$alkenyl, Ar-C$_{0-6}$alkyl, or Het-C$_{0-6}$alkyl;

each R$^5$ independently is H, C$_{1-6}$alkyl, C$_{2-6}$alkenyl, Ar-C$_{0-6}$alkyl, or Het-C$_{0-6}$alkyl;

R$^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;

R' is H, C$_{1-6}$alkyl, C$_{2-6}$alkenyl, Ar-C$_{0-6}$alkyl, or Het-C$_{0-6}$alkyl;

R" is C$_{1-6}$alkyl, Ar-C$_{0-6}$alkyl, Het-C$_{0-6}$alkyl, Ar-C$_{2-6}$alkenyl or Het-C$_{2-6}$alkenyl; and n is 1, 2 or 3;

or a pharmaceutically acceptable salt thereof, or (IV)

wherein:
R$^1$ is R", R"C(O), R"C(S), R"SO$_2$, R"OC(O), R"R'NC(O), or R"OC(O)NR'CH(R$^6$)C(O);

R$^2$ is H, C$_{1-6}$alkyl, C$_{2-6}$alkenyl, Ar-C$_{0-6}$alkyl, or Het-C$_{0-6}$alkyl;

R$^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;

R$^4$ is H, C$_{1-6}$alkyl, C$_{2-6}$alkenyl, Ar-C$_{0-6}$alkyl, or Het-C$_{0-6}$alkyl;

each R$^5$ independently is H, C$_{1-6}$alkyl, C$_{2-6}$alkenyl, Ar-C$_{0-6}$alkyl, or Het-C$_{0-6}$alkyl;

R$^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;

R' is H, C$_{1-6}$alkyl, C$_{2-6}$alkenyl, Ar-C$_{0-6}$alkyl, or Het-C$_{0-6}$alkyl;

R" is C$_{1-6}$alkyl, Ar-C$_{0-6}$alkyl, Het-C$_{0-6}$alkyl, Ar-C$_{2-6}$alkenyl or Het-C$_{2-6}$alkenyl; and n is 1, 2 or 3;

or a pharmaceutically acceptable salt thereof, or (V)

wherein:
R$^1$ is R", R"C(O), R"C(S), R"SO$_2$, R"OC(O), R"R'NC(O), or R"OC(O)NR'CH(R$^6$)C(O);

R$^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;

R$^4$ is H, C$_{1-6}$alkyl, C$_{2-6}$alkenyl, Ar-C$_{0-6}$alkyl, or Het-C$_{0-6}$alkyl;

each R$^5$ independently is H, C$_{1-6}$alkyl, C$_{2-6}$alkenyl, Ar-C$_{0-6}$alkyl, or Het-C$_{0-6}$alkyl;

R$^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;

R' is H, C$_{1-6}$alkyl, C$_{2-6}$alkenyl, Ar-C$_{0-6}$alkyl, or Het-C$_{0-6}$alkyl;

R" is C$_{1-6}$alkyl, Ar-C$_{0-6}$alkyl, Het-C$_{0-6}$alkyl, Ar-C$_{2-6}$alkenyl or Het-C$_{2-6}$alkenyl;

X is O or S; and n is 1, 2 or 3;

or a pharmaceutically acceptable salt thereof.

Representative intermediates of this invention are:

trans-4-(R,S)-Amino-N-[(benzyloxycarbonyl)-S-leucine]-3-hydroxytetrahydrofuran;

trans-4-(R,S)-Amino-N-[(tert-butoxycarbonyl)-S-leucine]-3-hydroxytetrahydrofuran;

trans-4-(R,S)-Amino-N-(S-leucine)-3-hydroxytetrahydrofuran;

trans-4-(R,S)-Amino-N-[(3,4-methylenedioxybenzoyl)-S-leucine]-3-hydroxytetrahydrofuran;

trans-4-(R,S)-Amino-N-[(3,4-dichlorobenzoyl)-S-leucine]-3-hydroxytetrahydrofuran;

trans-4-(R,S)-Amino-N-[(2-quinolinecarbonyl)-S-leucine]-3-hydroxytetrahydrofuran;

trans-4-(R,S)-Amino-N-[(benzyloxycarbonyl)-S-leucine]-3-hydroxytetrahydropyran;

trans-4-(R,S)-Amino-N-[(benzo[b]thiophen-2-ylcarbonyl)-S-leucine]-3-hydroxytetrahydropyran;

trans-4-(R,S)-Amino-N-[(benzo[b]thiophen-2-ylcarbonyl)-S-leucine]-3-hydroxytetrahydrofuran;

trans-4-(R,S)-Amino-N-[(indole-6-ylcarbonyl)-S-leucine]-3-hydroxytetrahydrofuran;

trans-4-(R,S)-Amino-N-[(5-aminobenzo[b]thiophen-2-ylcarbonyl)-S-leucine]-3-hydroxytetrahydrofuran trans-4-Amino-3-hydroxytetrahydrofuran;

trans-3-Hydroxy-4-benzyloxycarbonylamino-tetrahydrofuran;

4-Benzyloxycarbonylamino-tetrahydrofuran-3-one;

3,3-Dimethoxy-4-benzyloxycarbonylamino-tetrahydrofuran;

3,3-Dimethoxy-4-amino-tetrahydrofuran trans-4-S-Amino-3-R-hydroxytetrahydrofuran;

trans-4-S-Amino-N-[(benzyloxycarbonyl)-S-leucine]-3-R-hydroxytetrahydrofuran;

trans-4-S-Amino-N-(S-leucine)-3-R-hydroxytetrahydrofuran;

trans-4-S-Amino-N-[(3,4-dichlorobenzoyl)-S-leucine]-3-R-hydroxytetrahydrofuran;

trans-4-S-Amino-N-[(2-quinolinecarbonyl)-S-leucine]-3-R-hydroxytetrahydrofuran, trans-4-S-Amino-N-[(benzo[b]thiophen-2-ylcarbonyl)-S-leucine]-3-R-hydroxytetrahydrofuran;
trans-4-S-Amino-N-[(benzofuran-2-ylcarbonyl)-S-leucine]-3-R-hydroxytetrahydrofuran;
trans-4-S-Amino-N-[(2-naphthoyl)-S-leucine]-3-R-hydroxytetrahydrofuran;
trans-4-S-Amino-N-[(5-methoxybenzofuran-2-ylcarbonyl)-S-leucine]-3-R-hydroxytetrahydrofuran;
trans-4-S-Amino-N-[(5-chlorobenzo[b]thiophen-2-ylcarbonyl)-S-leucine]-3-R-hydroxytetrahydrofuran;
trans-4-S-Amino-N-[(4-chlorobenzo[b]thiophen-2-ylcarbonyl)-S-leucine]-3-R-hydroxytetrahydrofuran;
trans-4-S-Amino-N-[(4-bromobenzoyl)-S-leucine]-3-R-hydroxytetrahydrofuran;
trans-4-S-Amino-N-[(4-(pyrid-2-yl)benzoyl)-S-leucine]-3-R-hydroxytetrahydrofuran;
trans-4-S Amino-N-[(4-(pyrid-3-yl)benzoyl)-S-leucine]-3-R-hydroxytetrahydrofuran;
trans-4-S-Amino-N-[(3,4-dimethoxybenzoyl)-S-leucine]-3-R-hydroxytetrahydrofuran;
trans-4-Amino-3-hydroxytetrahydropyran;
trans-4-(R,S)-Amino-N-[(benzyloxycarbonyl)-S-leucine]-3-hydroxytetrahydropyran;
trans-4-(R,S)-Amino-N-(S-leucine)-3-hydroxytetrahydropyran;
trans-4-(R,S)-Amino-N-[(benzo[b]thiophen-2-ylcarbonyl)-S-leucine]-3-hydroxytetrahydropyran;
N-benzo[b]thiophene-2-ylcarbonyl-L-leucine methyl ester;
N-benzo[b]thiophene-2-ylcarbonyl-L-leucine;
N-benzo[b]thiophene-2-ylcarbonyl-L-leucine-S-(methoxycarbonylmethyl)-L,D-cysteine ethyl ester; and
2-Methoxycarbonyl-4-(R,S)-Amino-N-[(benzo[b]thiophene-2-ylcarbonyl)-S-leucine]-tetrahydrothiophene-3-one;
or salts thereof.

These intermediates are prepared using methods analogous to that described in Schemes 1–4 and the Examples described hereinafter.

Prodrugs of compounds of the present invention may be a prodrug of the ketone functionality of formula (I) compounds, specifically ketals or hemiketals, of the formula (VI):

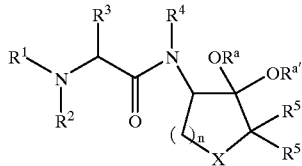

(VI)

wherein:
$R^1$ is R", R"C(O), R"C(S), R"SO$_2$, R"OC(O), R"R'NC(O), or R"OC(O)NR'CH(R$^6$)C(O);
$R^2$ is H, C$_{1-6}$alkyl, C$_{2-6}$alkenyl, Ar-C$_{0-6}$alkyl, or Het-C$_{0-6}$alkyl;
$R^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;
$R^4$ is H, C$_{1-6}$alkyl, C$_{2-6}$alkenyl, Ar-C$_{0-6}$alkyl, or Het-C$_{0-6}$alkyl;
each $R^5$ independently is H, C$_{1-6}$alkyl, C$_{2-6}$alkenyl, Ar-C$_{0-6}$alkyl, or Het-C$_{0-6}$alkyl;
$R^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;
R' is H, C$_{1-6}$alkyl, C$_{2-6}$alkenyl, Ar-C$_{0-6}$alkyl, or Het-C$_{0-6}$alkyl;
R" is C$_{1-6}$alkyl, Ar-C$_{0-6}$alkyl, Het-C$_{0-6}$alkyl, Ar-C$_{2-6}$alkenyl or Het-C$_{2-6}$alkenyl;
X is O or S;
n is 1, 2 or 3; and
$R^a$ and $R^{a'}$ independently are H or C$_{1-2}$alkyl, with the proviso that when one of $R^a$ and $R^{a'}$ is H, the other is C$_{1-2}$alkyl; or together are (CH$_2$)$_{2-3}$ forming a 5- or 6-membered ring;
or a pharmaceutically acceptable salt thereof.

Abbreviations and symbols commonly used in the peptide and chemical arts are used herein to describe the compounds of the present invention. In general, the amino acid abbreviations follow the IUPAC-IUB Joint Commission on Biochemical Nomenclature as described in *Eur. J. Biochem.*, 158, 9 (1984). The term "amino acid" as used herein refers to the D- or L-isomers of alanine, arginine, asparagine, aspartic acid, cysteine, glutamine, glutamic acid, glycine, histidine, isoleucine, leucine, lysine, methionine, phenylalanine, proline, serine, threonine, tryptophan, tyrosine and valine.

"C$_{1-6}$alkyl" as applied herein is meant to include substituted and unsubstituted methyl, ethyl, n-propyl, isopropyl, n-butyl, isobutyl and t-butyl, pentyl, n-pentyl, isopentyl, neopentyl and hexyl and the simple aliphatic isomers thereof. Any C$_{1-6}$alkyl group may be optionally substituted independently by one or two halogens, SR', OR', N(R')$_2$, C(O)N(R')$_2$, carbamyl or C$_{1-4}$alkyl, where R' is H or C$_{1-6}$alkyl. C$_0$alkyl means that no alkyl group is present in the moiety. Thus, Ar-C$_0$alkyl is equivalent to Ar.

"C$_{3-6}$cycloalkyl" as applied herein is meant to include substituted (i.e., alkyl, OR, SR or halogen) and unsubstituted cyclopropane, cyclobutane, cyclopentane, and cyclohexane.

"C$_{2-6}$alkenyl" as applied herein means an alkyl group of 2 to 6 carbons, wherein a carbon-carbon single bond is replaced by a carbon-carbon double bond. C$_{2-6}$alkenyl includes ethylene, 1-propene, 2-propene, 1-butene, 2-butene, isobutene and the several isomeric pentenes and hexenes. Both cis and trans isomers are included.

"C$_{2-6}$alkynyl" means an alkyl group of 2 to 6 carbons, wherein one carbon-carbon single bond is replaced by a carbon-carbon triple bond. C$_{2-6}$alkynyl includes acetylene, 1-propyne, 2-propyne, 1-butyne, 2-butyne, 3-butyne, and the simple isomers of pentyne and hexyne.

"Halogen" or "halo" means F, Cl, Br, and I.

"Ar" or "aryl" means unsubstituted phenyl or naphthyl; or phenyl or naphthyl substituted by one or more of Ph-C$_{0-6}$alkyl, Het-C$_{0-6}$alkyl, C$_{1-6}$alkoxy, Ph-C$_{0-6}$alkoxy, Het-C$_{0-6}$alkoxy, OH, (CH$_2$)$_{1-6}$NR'R', O(CH$_2$)$_{1-6}$NR'R'; wherein each R' independently is H, C$_{1-6}$alkyl, Ar-C$_{0-6}$alkyl, or Het-C$_{0-6}$alkyl; or phenyl or naphthyl substituted by one to three moieties selected from C$_{1-4}$alkyl, OR', N(R')$_2$, SR', CF$_3$, NO$_2$, CN, CO$_2$R', CON(R')$_2$, F, Cl, Br and I, or substituted by a methylenedioxy group.

As used herein "Het" or "heterocyclic" represents a stable 5- to 7-membered monocyclic or a stable 7- to 10-membered bicyclic heterocyclic ring, which is either saturated or unsaturated, and which consists of carbon atoms and from one to four heteroatoms selected from the group consisting of N, O and S, and wherein the nitrogen and sulfur heteroatoms may optionally be oxidized, and the nitrogen heteroatom may optionally be quaternized, and including any bicyclic group in which any of the above-defined heterocyclic rings is fused to a benzene ring. The heterocyclic ring may be attached at any heteroatom or carbon atom which results in the creation of a stable structure, and may optionally be substituted with one or two moieties selected from $C_{1-4}$alkyl, OR', N(R')$_2$, SR', CF$_3$, NO$_2$, CN, CO$_2$R', CON(R')$_2$, F, Cl, Br and I, where R' is as defined herein before. Examples of such heterocycles include piperidinyl, piperazinyl, 2-oxopiperazinyl, 2-oxopiperidinyl, 2-oxopyrrolodinyl, 2-oxoazepinyl, azepinyl, thienyl, pyrrolyl, 4-piperidonyl, pyrrolidinyl, pyrazolyl, pyrazolidinyl, imidazolyl, pyridyl, pyrazinyl, oxazolidinyl, oxazolinyl, oxazolyl, isoxazolyl, morpholinyl, thiazolidinyl, thiazolinyl, isothiazolyl, thiazolyl, quinuclidinyl, indolyl, quinolinyl, isoquinolinyl, benzimidazolyl, benzothienyl, benzopyranyl, benzoxazolyl, benzofuranyl, furyl, pyranyl, tetrahydrofuryl, tetrahydropyranyl, thienyl, benzoxazolyl, thiamorpholinyl sulfoxide, thiamorpholinyl sulfone, oxadiazolyl, benzothiazolyl, benzoisothiazolyl, benzisoxazolyl, pyrimidinyl, cinnolinyl, quinazolinyl, quinoxalinyl, 1,5-napthyridinyl, 1,6napthyridinyl, 1,7-napthyridinyl, 1,8-napthyridinyl, tetrazolyl, 1,2,3-triazolyl, and 1,2,4-triazolyl.

Certain radical groups are abbreviated herein. t-Bu refers to the tertiary butyl radical; Boc or BOC refers to the tbutyloxycarbonyl radical; Fmoc refers to the fluorenylmethoxycarbonyl radical; Ph refers to the phenyl radical; and Cbz or CBZ refers to the benzyloxycarbonyl radical.

Certain reagents are abbreviated herein. DCC refers to dicyclohexylcarbodiimide; EDC or EDCI refers to N-ethyl-N'(dimethylaminopropyl)-carbodiimide. HOBT or HOBt refers to 1-hydroxybenzotriazole; DMF refers to dimethyl formamide; DIEA refers to di-isopropylethylamine; Lawesson's reagent is 2,4-bis(4-methoxyphenyl)-1,3-dithia-2,4-diphosphetane-2,4-disulfide; TFA refers to trifluoroacetic acid; and THF refers to tetrahydrofuran.

Compounds of the formula (I) are generally prepared by:

(i) reacting a compound of the formula (III):

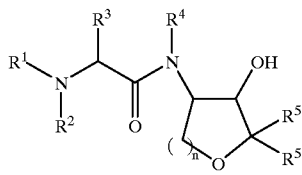

(III)

wherein $R^1$, $R^2$, $R^3$, $R^4$, $R^5$ and n are as defined in formula (I), with any reactive functional groups protected, with an oxidizing agent; or (ii) decarboxylating a compound of the formula (IV):

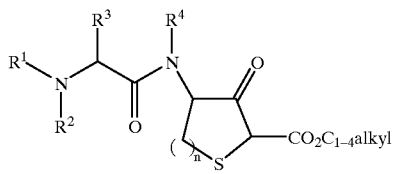

(IV)

wherein $R^1$, $R^2$, $R^3$, $R^4$, $R^5$ and n are as defined in formula (I), with any reactive functional groups protected; or (iii) reacting a compound of the formula (V):

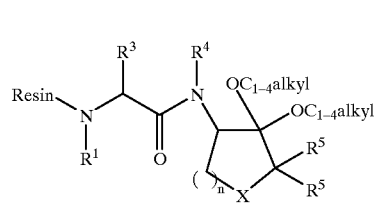

(V)

wherein $R^1$, $R^3$, $R^4$, $R^5$ and n are as defined in formula (I), with any reactive functional groups protected, with an acid; and thereafter removing any protecting groups and optionally forming a pharmaceutically acceptable salt.

Compounds of the formula (I) are prepared by methods analogous to those described in the solution synthesis method of Scheme 1, or the solid support method of Scheme 2, or the solution synthesis method of Scheme 3.

Scheme 1

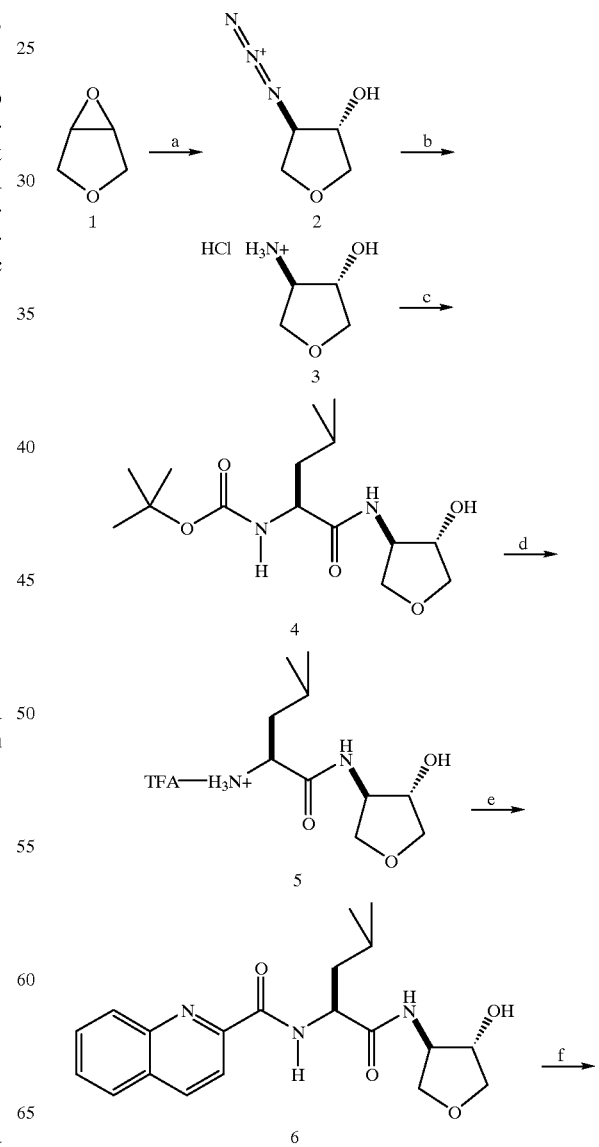

13
-continued

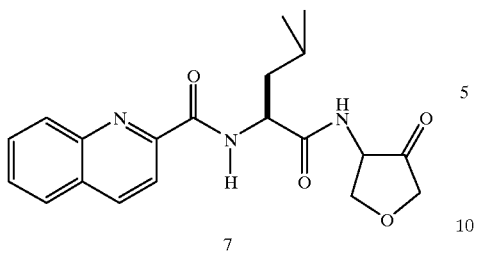

7 a) NaN₃, ammonium chloride, methanol:water; b) 10% Pd/C, EtOH, H₂; ethanolic HCl; c) trimethylacetyl chloride, N-BOC-leucine, DIEA, CH₂Cl₂; d) TFA, CH₂Cl₂; e) RCOCl, sodium hydrogen carbonate, 1,4-dioxane; f) Dess-Martin periodinane, CH₂Cl₂

Compounds of the general formula (I), wherein n is 1 and $R^1$ is R"C(O) are prepared by methods shown in Scheme 1. Treatment of the known epoxide 1-Scheme-1 with sodium azide and ammonium chloride in aqueous methanol at elevated temperatures provides the azide 2-Scheme-1. Reduction of the azide 2-Scheme-1 utilizing methods that are known in the art, such as reduction with palladium on carbon in ethanol under an atmosphere of hydrogen, provides the amine salt 3-Scheme-1 after treatment with ethanolic hydrogen chloride. The amine salt 3-Scheme-1 may be coupled with a carboxylic acid by methods that are known in the art, such as acylation with an acid chloride or coupling with an acid in the presence of EDC and HOBT, to provide the amide 4-Scheme-1. The tert-butoxycarbonyl group may be removed by treatment with a strong acid, such as TFA, in an aprotic solvent, such as dichloromethane, to provide 5-Scheme-1. The salt 5-Scheme-1 may be acylated with an acid chloride in 1,4-dioxane in the presence of an aqueous base, such as saturated sodium hydrogen carbonate, to yield 6-Scheme-1. The alcohol 6-Scheme-1 may be oxidized by methods known in the art, such as by treatment with Dess-Martin periodinane, in an aprotic solvent, such as dichloromethane.

Scheme 2

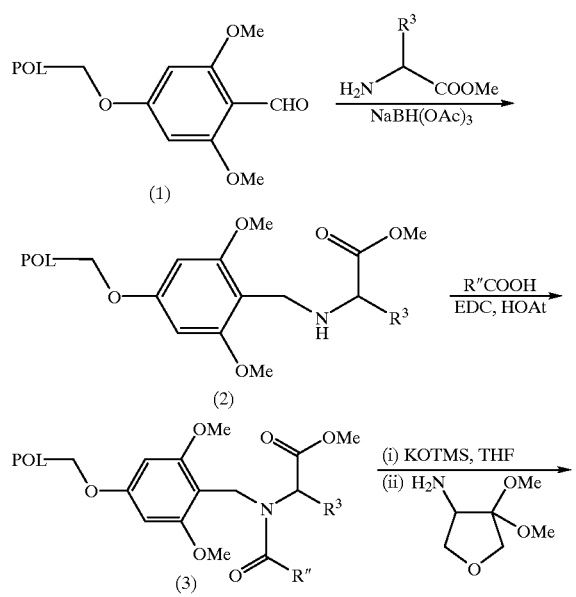

14
-continued

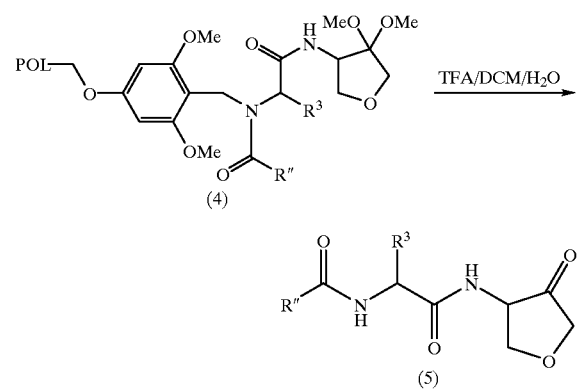

Compounds of the general formula (I), wherein $R^1$ is C(O)R', $R^2$ is H, $R^4$ is H, $R^5$ is H, X is O, and n is 1, are prepared by the solid support synthesis (SPS) method shown in Scheme 2. In particular, in the first step, sodium triacetoxyborohydride is added to a stirred solution of Ellmans resin in DMF containing 1% HOAc, and then the α-amino acid, methyl ester is added to give rise to 2-Scheme-2. The amine group is coupled with a carboxylic acid by using known methods, such as by the addition of the carboxylic acid with EDC, to give rise to the amide, 3-Scheme-2. Thereafter, the ester group is hydrolysed, for example, with potassium trimethylsilanoate in THF, and the liberated acid group is coupled with 3,3-dimethoxy-4-aminotetrahydofuran using, for example, EDC in NMP, to give rise to 4-Scheme-2. The blocking group is then removed by known cleaving methods, such as by the addition of 7:2:1 TFA/CH₂Cl₂/H₂O, to give rise to the desired compound, 5-Scheme-2.

Compounds of the general formula (I), wherein $R^1$ is C(O)R', $R^2$ is H, $R^4$ is H, $R^5$ is H, X is O, and n is 2, are prepared by the solid support synthesis (SPS) method shown in Scheme 2, except 3,3-dimethoxy-4-aminotetrahydropyran is substituted for 3,3-dimethoxy-4-amino-tetrahydofuran.

Scheme 3

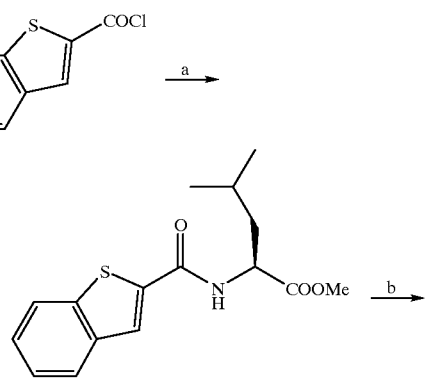

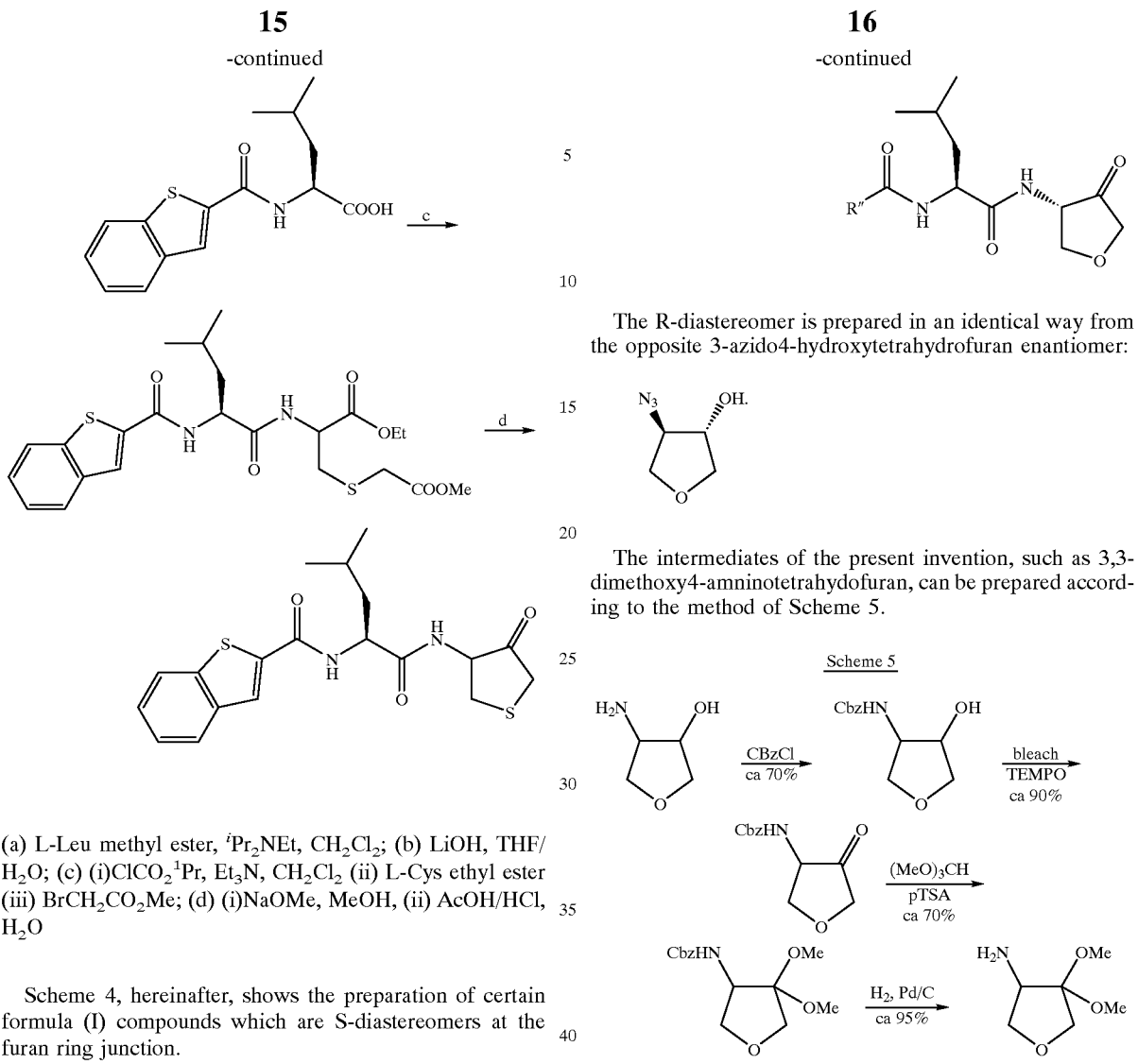

(a) L-Leu methyl ester, $^iPr_2NEt$, $CH_2Cl_2$; (b) LiOH, THF/$H_2O$; (c) (i)$ClCO_2{}^iPr$, $Et_3N$, $CH_2Cl_2$ (ii) L-Cys ethyl ester (iii) $BrCH_2CO_2Me$; (d) (i)NaOMe, MeOH, (ii) AcOH/HCl, $H_2O$ Scheme 4, hereinafter, shows the preparation of certain formula (I) compounds which are S-diastereomers at the furan ring junction.

Scheme 4

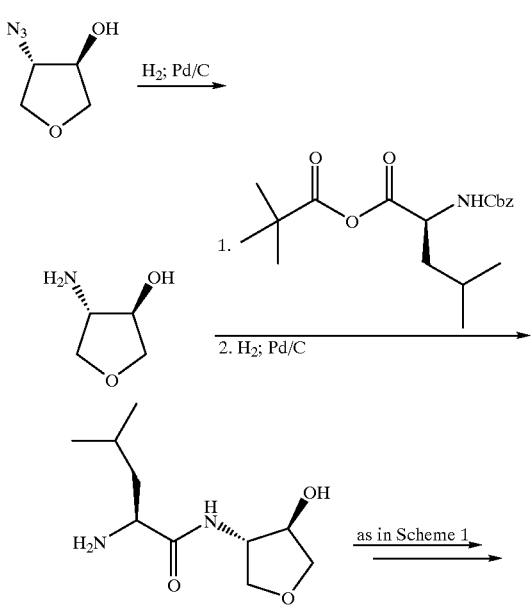

The R-diastereomer is prepared in an identical way from the opposite 3-azido4-hydroxytetrahydrofuran enantiomer:

The intermediates of the present invention, such as 3,3-dimethoxy4-amninotetrahydofuran, can be prepared according to the method of Scheme 5.

The steps in Scheme 5 are presented as follows. First, a nitrogen-protecting group is added by reacting 3-hydroxy4-aminotetrahydofuran with benzychloroformate in dioxane containing aqueous sodium carbonate. Thereafter, the alcohol group is oxidized by known methods, such as by the addition of bleach containing sodium bicarbonate in the presence of sodium bromide and TEMPO in EtOAc, toluene, and water, to give rise to the ketone. The ketone is converted to the dimethylketal by the addition of trimethyl-orthoformate in the presence of paratoluenesulphonic acid in methanol. Finally, the protecting group is removed by hydrogenation using, for example, palladium an charcoal in the presence of ethanol under an atmosphere of hydrogen. excessive bone or cartilage loss, including osteoporosis, gingival disease including gingivitis and periodontitis, arthritis, more specifically, osteoarthritis and rheumatoid arthritis, Paget's disease; hypercalcemia of malignancy, and metabolic bone disease.

Metastatic neoplastic cells also typically express high levels of proteolytic enzymes that degrade the surrounding matrix, and certain tumors and metastatic neoplasias may be effectively treated with the compounds of this invention.

The present invention also provides methods of treatment of diseases caused by pathological levels of proteases, particularly cysteine and serine proteases, more particularly cysteine proteases, even more particularly as inhibitors of cysteine proteases of the papain superfamily, yet more particularly cysteine proteases of the cathepsin family, which methods comprise administering to an animal, particularly a mammal, most particularly a human in need thereof a compound of the present invention. The present invention especially provides methods of treatment of diseases caused by pathological levels of cathepsin K, which methods comprise administering to an animal, particularly a mammal, most particularly a human in need thereof, an inhibitor of cathepsin K, including a compound of the present invention. The present invention particularly provides methods for treating diseases in which cysteine proteases are implicated, including infections by pneumocystis carinii, trypsanoma cruzi, trypsanoma brucei, and Crithidia fusiculata; as well as in schistosomiasis, malaria, tumor metastasis, metachromatic leukodystrophy, muscular dystrophy, amytrophy, and especially diseases in which cathepsin K is implicated, most particularly diseases of excessive bone or cartilage loss, including osteoporosis, gingival disease including gingivitis and periodontitis, arthritis, more specifically, osteoarthritis and rheumatoid arthritis, Paget's disease, hypercalcemia of malignancy, and metabolic bone disease.

This invention further provides a method for treating osteoporosis or inhibiting bone loss which comprises internal administration to a patient of an effective amount of a compound of formula (I), alone or in combination with other inhibitors of bone resorption, such as bisphosphonates (i.e., allendronate), hormone replacement therapy, anti-estrogens, or calcitonin. In addition, treatment with a compound of this invention and an anabolic agent, such as bone morphogenic protein, iproflavone, may be used to prevent bone loss or to increase bone mass.

In accordance with this invention, an effective amount of the compounds of formula (I) is administered to inhibit the protease implicated with a particular condition or disease. Of course this dosage amount will further be modified according to the type of administration of the compound. For example, "effective amount" for acute therapy, parenteral administration of a compound of formula (I) is preferred. An intravenous infusion of the compound in 5% dextrose in water or normal saline, or a similar formulation with suitable excipients, is most effective, although an intramuscular bolus injection is also useful. Typically, the parenteral dose will be about 0.01 to about 100 mg/kg; preferably between 0.1 and 20 mg/kg, in a manner to maintain the concentration of drug in the plasma at a concentration effective to inhibit cathepsin K. The compounds are administered one to four times daily at a level to achieve a total daily dose of about 0.4 to about 400 mg/kg/day. The precise amount of an inventive compound which is therapeutically effective, and the route by which such compound is best administered, is readily determined by one of ordinary skill in the art by comparing the blood level of the agent to the concentration required to have a therapeutic effect.

Prodrugs of compounds of the present invention may be prepared by any suitable method. For those compounds in which the prodrug moiety is a ketone functionality, specifically ketals and/or hemiacetals, the conversion may be effected in accordance with conventional methods.

The compounds of this invention may also be administered orally to the patient, in a manner such that the concentration of drug is sufficient to inhibit bone resorption or to achieve any other therapeutic indication as disclosed herein. Typically, a pharmaceutical composition containing the compound is administered at an oral dose of between about 0.1 to about 50 mg/kg in a manner consistent with the condition of the patient. Preferably the oral dose would be about 0.5 to about 20 mg/kg.

No unacceptable toxicological effects are expected when compounds of the present invention are administered in accordance with the present invention.

The compounds of this invention may be tested in one of several biological assays to determine the concentration of a compound which is required to have a given pharmacological effect.

Determination of Cathepsin K Proteolytic Catalytic Activity

All assays for cathepsin K were carried out with human recombinant enzyme. Standard assay conditions for the determination of kinetic constants used a fluorogenic peptide substrate, typically Cbz-Phe-Arg-AMC, and were determined in 100 mM Na acetate at pH 5.5 containing 20 mM cysteine and 5 mM EDTA. Stock substrate solutions were prepared at concentrations of 10 or 20 mM in DMSO with 20 $\mu$M final substrate concentration in the assays. All assays contained 10% DMSO. Independent experiments found that this level of DMSO had no effect on enzyme activity or kinetic constants. All assays were conducted at ambient temperature. Product fluorescence (excitation at 360 nM; emission at 460 nM) was monitored with a Perceptive Biosystems Cytofluor II fluorescent plate reader. Product progress curves were generated over 20 to 30 minutes following formation of AMC product.

Inhibition Studies

Potential inhibitors were evaluated using the progress curve method. Assays were carried out in the presence of variable concentrations of test compound. Reactions were initiated by addition of enzyme to buffered solutions of inhibitor and substrate. Data analysis was conducted according to one of two procedures depending on the appearance of the progress curves in the presence of inhibitors. For those compounds whose progress curves were linear, apparent inhibition constants ($K_{i,app}$) were calculated according to equation 1 (Brandt et al., *Biochemitsry*, 1989, 28, 140):

$$v=V_m A/[K_a(1+I/K_{i,app})+A] \quad (1)$$

where v is the velocity of the reaction with maximal velocity $V_m$, A is the concentration of substrate with Michaelis constant of $K_a$, and I is the concentration of inhibitor.

For those compounds whose progress curves showed downward curvature characteristic of time-dependent inhibition, the data from individual sets was analyzed to give $k_{obs}$ according to equation 2:

$$[AMC]=v_{SS}t+(v_0-v_{SS})[1-exp(-k_{obs}t)]/k_{obs} \quad (2)$$

where [AMC] is the concentration of product formed over time t, $v_0$ is the initial reaction velocity, and $v_{SS}$ is the final steady state rate. Values for $k_{obs}$ were then analyzed as a linear function of inhibitor concentration to generate an apparent second order rate constant ($k_{obs}$/inhibitor concentration or $k_{obs}/[I]$) describing the time-dependent inhibition. A complete discussion of this kinetic treatment has been fully described (Morrison et al., *Adv. Enzymol. Relat. Areas Mol. Biol.*, 1988, 61, 201).

One skilled in the art would consider any compound with a $K_i$ of less than 50 micromolar to be a potential lead compound. Preferably, the compounds used in the method of the present invention have a $K_i$ value of less than 1 micromolar. Most preferably, said compounds have a $K_i$ value of less than 100 nanomolar. 4-(R,S)-Amino-N-[(8-quinolinesulfonyl)-S-leucine]-3-tetrahydrofuran-3-one, a compound of formula (I), has a $K_i$ value that is greater than 10 micromolar.

Human Osteoclast Resorption Assay

Aliquots of osteoclastoma-derived cell suspensions were removed from liquid nitrogen storage, warmed rapidly at 37° C. and washed ×1 in RPMI-1640 medium by centrifugation (1000 rpm, 5 min at 4° C.). The medium was aspirated and replaced with murine anti-HLA-DR antibody, diluted 1:3 in RPMI-1640 medium, and incubated for 30 minutes on ice. The cell suspension was mixed frequently.

The cells were washed ×2 with cold RPMI-1640 by centrifugation (1000 rpm, 5 min at 4° C.) and then transferred to a sterile 15 mL centrifuge tube. The number of mononuclear cells were enumerated in an improved Neubauer counting chamber.

Sufficient magnetic beads (5/mononuclear cell), coated with goat anti-mouse IgG, were removed from their stock bottle and placed into 5 mL of fresh medium (this washes away the toxic azide preservative). The medium was removed by immobilizing the beads on a magnet and is replaced with fresh medium.

The beads were mixed with the cells and the suspension was incubated for 30 minutes on ice. The suspension was mixed frequently. The bead-coated cells were immobilized on a magnet and the remaining cells (osteoclast-rich fraction) were decanted into a sterile 50 mL centrifuge tube. Fresh medium was added to the bead-coated cells to dislodge any trapped osteoclasts. This wash process was repeated ×10. The bead-coated cells were discarded.

The osteoclasts were enumerated in a counting chamber, using a large-bore disposable plastic pasteur pipette to charge the chamber with the sample. The cells were pelleted by centrifugation and the density of osteoclasts adjusted to $1.5 \times 10^4$/mL in EMEM medium, supplemented with 10% fetal calf serum and 1.7 g/liter of sodium bicarbonate. 3 mL aliquots of the cell suspension ( per treatment) were decanted into 15 mL centrifuge tubes. These cells were pelleted by centrifugation. To each tube 3 mL of the appropriate treatment was added (diluted to 50 $\mu$M in the EMEM medium). Also included were appropriate vehicle controls, a positive control (87MEM1 diluted to 100 ug/mL) and an isotype control (IgG2a diluted to 100 ug/mL). The, tubes were incubated at 37° C. for 30 minutes.

0.5 mL aliquots of the cells were seeded onto sterile dentine slices in a 48-well plate and incubated at 37° C. for 2 hours. Each treatment was screened in quadruplicate. The slices were washed in six changes of warm PBS (10 mL/well in a 6-well plate) and then placed into fresh treatment or control and incubated at 37° C. for 48 hours. The slices were then washed in phosphate buffered saline and fixed in 2% glutaraldehyde (in 0.2M sodium cacodylate) for 5 minutes, following which they were washed in water and incubated in buffer for 5 minutes at 37° C. The slices were then washed in cold water and incubated in cold acetate buffer/fast red garnet for 5 minutes at 4° C. Excess buffer was aspirated, and the slices were air dried following a wash in water.

The TRAP positive osteoclasts were enumerated by bright-field microscopy and were then removed from the surface of the dentine by sonication. Pit volumes were determined using the Nikon/Lasertec ILM21W confocal microscope.

EXAMPLES

In the following synthetic examples, unless otherwise indicated, all of the starting materials were obtained from commercial sources. Without further elaboration, it is believed that one skilled in the art can, using the preceeding description, utilize the present invention to its fullest extent. These Examples are given to illustrate the invention, not to limit its scope. Reference is made to the claims for what is reserved to the inventors hereunder.

Example 1

Preparation of 4-(R,S)-Amino-N-[(3,4-methylenedioxybenzoyl)-S-leucine]-tetrahydrofuran-3-one a) trans-4-Azido-3-hydroxy tetrahydrofuran 3,4-Epoxytetrahydrofuran (9 g, 105 mmol) was added to a stirred solution of sodium azide (27 g, 415 mmol) and ammonium chloride (9 g, 159 mmol) in aqueous methanol (95%, 200 ml). The reaction was heated to 75° C. and stirred for 20 hours. The reaction was cooled, filtered and evaporated under reduced pressure. The residue was diluted with water and extracted with ethyl acetate, dried and evaporated under reduced pressure to afford the title compound as a colourless oil, 10 g, 74% yield.

[1] H NMR δ(CDCl$_3$) 4.32 (m, 1H), 4.09 (dd, 1H, J=4.8, 9.9 Hz), 3.99 (dd, 1H, J=4.3, 10.1 Hz). 3.94 (m, 1H), 3.81 (dd, 1H, J=2.1, 9.9 Hz), 3.73 (dd, 1H, J=1.8, 10.1 Hz), 2.72 (d, 1H, J=4.6 Hz).

b) trans-4-Amino-3-hydroxytetrahydrofuran hydrochloride

A mixture of trans-4-azido-3-hydroxytetrahydrofuran (10 g, 77 mmol) and 10% palladium on charcoal (1 g) in ethanol (150 ml) was stirred under an atmosphere of hydrogen (35 psi) for 12 hours. The mixture was filtered and treated with 100 ml of ethanolic HCl to afford, after evaporation under reduced pressure, the title compound as a brown solid, 10.5 g, 97% yield. m.p. 132° C.

[1] H NMR δ(d$_6$ DMSO) 8.37 (s, 3H), 4.13 (m, 1H), 3.84 (dd, 1H, J=4.9 and 14.3), 3.76 (dd, 1H, J=5.5, 10.0 Hz), 3.58 (dd, 1H, J=2.7, 10.0 Hz), 3.34 (m, 3 H).

c) trans-4-(R,S) -Amino-N-[(tert-butoxycarbonyl)-S-leucine]-3-hydroxytetrahydrofuran Trimethylacetyl chloride (3.5 ml, 29 mmol) was added to a stirred solution of N-Boc-L-leucine (7.3 g, 31 mmol) and diisopropylethylamine (9 ml, 52 mmol) in dichloromethane (200 ml). After 1 h, trans-4-amino-3-hydroxytetrahydrofuran. HCl (4 g, 28 mmol) was added and the mixture was allowed to stir overnight. The reaction mixture was poured into water and extracted with dichloromethane. The combined organic layers were washed with 0.5N HCl, saturated sodium hydrogen carbonate, brine and dried. Evaporation under reduced pressure afforded the title compound as a yellow foam, 5 g, 44% yield.

$^1$H NMR δ(CDCl$_3$) 8.08 (d, 0.5H, J=4.8 Hz), 7.89 (d, 0.5H, J=7.4 Hz), 6.20 (d, 0.5H, J=8.3 Hz), 6.09 (δ, 0.5H, J=8.7 Hz), 4.81 (d, 1H, J=16.0 Hz), 4.40 (m, 2H), 4.20 (m, 2H), 3.77 (m, 2H), 1.60 (m, 3H), 1.50 (s, 9H), 0.92 (m, 6H).

d) trans-4-(R,S)-Amino-N-(S-leucine)-3-hydroxytetrahydrofuran. TFA salt trans-4Amino-N-[(tert-butoxycarbonyl)-S-leucine]-3-hydroxytetrahydrofuran (2.5 g, 8.0 mmol) was added to a stirred solution of 20% trifluoroacetic acid in dichloromethane (100 ml). After 2 hours, the reaction mixture was evaporated under reduced pressure to afford the title compound as a white gum, 2.6 g, 100% yield.

$^1$H NMR δ(MeOD) 4.18 (m, 2H), 4.08 (m, 2H), 3.97 (m, 2H), 3.86 (apparent t, 2H, J=7.1 Hz), 3.69 (dd, 2H, J=1.6, 7.4 Hz), 1.68 (m, 3H), 0.99 (d, 6H, J=2.1 Hz).

e) trans4-(R,S)-Amino-N-[(3,4-methylenedioxybenzoyl)-S-leucine]-3-hydroxytetrahydrofuran Piperonyloyl chloride (400 mg, 2.2 mmol) was added to a stirred solution of trans-4-amino-N-(S-leucine)-3-hydroxytetrahydrofuran. TFA salt (380 mg, 1.1 mmol) in saturated sodium hydrogen carbonate (10 ml) and 1,4 dioxane (10 ml). The reaction was allowed to stir for 1 hour then diluted with ether. The organic layer was washed with 1N hydrochloric acid, sodium hydrogen carbonate, brine and dried. Evaporation of the solvent gave the title compound as a white foam, 250 mg, 60% yield.
$^1$H NMR δ(CDCl$_3$) 8.23 (d, 0.5H, J=4.8 Hz), 8.15 (d, 0.5H, J=7.4 Hz), 7.85 (d, 0.5H, J=7.6 Hz), 7.3 (m, 2 H), 6.66 (dd, 1H, J=8.1, 11.5 Hz), 5.92 (d, 2H, J=6.2 Hz), 4.78 (m, 1H), 4.50 (s, 1H), 4.2 (s, 1H), 4.08-3.75 (m, 4H), 3.74-3.48 (m, 3H), 1.82-1.48 (m, 3H), 0.90 (m, 6H).
MS calcd for (C$_{18}$H$_{24}$N$_2$O$_5$+H)$^+$: 365. Found: 365.

f) 4(R,S)-Amino-N-[(3,4-methylenedioxybenzoyl)-S-leucine]-tetrahydrofuran-3-one

Dess-Martin periodinane (500 mg, 1.2 mmol) was added to a stirred solution of trans-4-(R,S)-amino-N-[(3,4-methylenedioxybenzoyl)-S-leucine]-3-hydroxytetrahydrofuran (220 mg, 0.60 mmol) in dichloromethane (10 ml). After 1 hour, ether was added followed by sodium thiosulfate (570 mg, 3.6 mmol). After an additional 15 minutes, the reaction was washed with saturated sodium hydrogen carbonate, brine and dried. Evaporation of the solvent gave the title compound as a white foam, 200 mg, 100% yield.
$^1$H NMR δ(CDCl$_3$) 8.14 (d, 0.5H, J=6.2 Hz), 7.90 (d, 0.5H, J=5.9 Hz), 7.54 (d, 0.5H, J=7.3 Hz), 7.46 (d, 0.5H, J=5.1 Hz), 7.23 (d, 1H, J=6.6 Hz), 7.14 (s, 1H), 6.67 (m, 1H), 5.93 (s, 2H), 4.73 (m, 1H), 4.37-3.71 (m, 5H), 1.68 (m, 3H), 0.85 (m, 6H).
MS calcd for (C$_{18}$H$_{24}$N$_2$O$_5$+H)$^+$: 363. Found: 363.

Example 2
Preparation of 4-(R,S)-Amino-N-[(3,4-dichlorobenzoyl)-S-leucine]-tetrahydrofuran-3-one Following the procedure of Example 1(e-f) except substituting 3,4-dichlorobenzoyl chloride for piperonyloyl chloride the title compound was prepared: $^1$H NMR δ(MeOD) 8.01 (d, 1H, J=2.0 Hz), 7.75 (dd, 1H, J=2.0, 8.3 Hz), 7.61 (d, 1H, J=8.3 Hz), 4.60 (m, 1H), 4.50-3.84 (m, 5H), 1.66 (m, 3H), 1.00 (m, 6H).
MS calcd for (C$_7$Cl$_2$H$_{20}$N$_2$O$_4$+H)$^-$: 387 & 389, Found: 387 & 389.

Example 3
Preparation of 4(R,S)-Amino-N-[(2-quinolinecarbonyl)-S-leucine]-tetrahydrofuran-3-one Following the procedure of Example 1(e-f) except substituting 2-quinolinecarbonyl chloride for piperonyloyl chloride, the title compound was prepared as a white foam: $^1$H NMR δ(CDCl$_3$) 8.57 (dd, 1H, J=1.5, 5.1 Hz), 8.20 (m, 3H), 7.77 (m, 2H), 7.62 (m, 1H), 7.40 (d, 1H, J=6.2 Hz), 4.80 (m, 1H), 4.57 (m, 1H), 4.30 (m, 1H), 4.26-3.87 (m, 3H), 1.96-1.71 (m, 3H), 1.00 (m, 6H).
MS calcd for (C$_{30}$H$_{23}$N$_3$O$_4$+H)$^+$: 370 Found: 370.

Example 4
Preparation of 4-(R,S)-Amino-N-[(benzyloxycarbonyl)-S-leucine]-tetrahydrofuran-3-one Following the procedure of Example 1 except substituting N-CBZ-leucine for N-BOC-leucine the title compound was prepared as a white foam: $^1$H NMR δ(CDCl$_3$) 7.31 (m, 5H), 5.71 (app dd, 1H, J=8.4, 14.8 Hz), 5.06 (m, 2H), 4.50 (dd, 1H, J=8.9, 18.0 Hz), 4.30-3.88 (m, 4H), 3.80 (app t, 1H, J=9.6 Hz), 1.64 (m, 3H), 0.91 (m, 6H).
MS calcd for (C$_{18}$H$_{24}$N$_2$O$_5$+H)$^+$: 349. Found: 349.

Example 5
Preparation of 4-(R,S)-Amino-N-[(3,4-methylenedioxybenzoyl)-S-leucine]-tetrahydrofuran-3-one Following the procedure of Example 1 except substituting 3,4-methylenedioxybenzoyl chloride for piperonyloyl chloride, the title compound was prepared.

Example 6
Preparation of 4-(R,S)-Amino-N-[(8-quinolinecarbonyl)-S-leucine]-tetrahydrofuran-3-one Following the procedure of Example 1(e-f) except substituting 8-quinolinecarbonyl chloride for piperonyloyl chloride, the title compound was prepared as a white foam: m.p. 123° C. (HCl salt).
$^1$H NMR δ(CDCl$_3$) 11.54 (m, 1H), 8.84 (d, 1H, J=1.5 Hz), 8.65 (d, 1H, J=7.2 Hz), 8.17 (d, 1H, J=8.0 Hz), 7.86 (d, 1H, J=8.0Hz), 7.7 (s, 1H), 7.54 (t, 1H, J=7.7 Hz), 7.40 (dd, 1H, J=3.8, 7.7 Hz), 4.78 (dd, 1H, J=7.5, 13.6 Hz), 4.47 (dd, 1H, J=8.6, 13.6 Hz), 4.18 (m, 1H), 4.16-3.79 (m, 3H), 1.88 (m, 3H), 0.88 (m, 6H).
MS calcd for (C$_{20}$H$_{23}$N$_3$O$_4$+H)$^+$: 370. Found: 370.

Example 7
Preparation of 4-(R,S)-Amino-N-[(8-quinolinesulfonyl)-S-leucine]-tetrahydrofuran-3-one Following the procedure of Example 1(e-f) except substituting 8-quinolinesulfonyl chloride for piperonyloyl chloride, the title compound was prepared as a brown solid: m.p. 98° C. (HCl salt).
$^1$H NMR δ(CDCl$_3$) 9.07 (dd, 1H1., J=1.7 and 4.3 Hz), 8.40 (m, 1H), 8.30 (m, 1H), 8.00 (m, 1H), 7.66 (m, 2H), 7.11 (d, 0.5H, J=5.9 Hz), 6.96 (d, 0.5H, J=5.7 Hz), 4.51 (t, 0.5H, d=8.8 Hz), 4.39 (t, 0.5H, J=8.7), 4.12-3.71 (m, 4.5H), 3.53 (dd, 0.5H, J=1.0, 5.9 Hz), 1.43 (m, 2H), 0.64 (m, 3H), 0.33 (m, 3H).
MS calcd for (C$_{19}$H$_{23}$N$_3$O$_5$S+H)$^+$: 406. Found: 406.

Example 8
Preparation of 4-(R,S)-Amino-N-[((4-methyl-3-pyridinyl)carbonyl)-S-leucine]-tetrahydrofuran-3-one Following the procedure of Example 1(e-f) except substituting (4-methyl-3-pyridinyl)carbonyl chloride for piperonyloyl chloride, the title compound was prepared.

Example 9
Preparation of 4-(R,S)-Amino-N-[(benzyloxycarbonyl)-S-leucine]-2,2-dibenzyl-tetrahydrofuran-3-one Sodium methoxide (140 mg, 2.6 mmol) was added to a stirred solution of 4-(R,S)-amino-N-[(benzyloxycarbonyl)-S-leucine]-tetrahydrofuran-3-one (300 mg, 0.9 mmol) and benzyl bromide (0.4 ml, 3.4 mmol) in methanol (5 ml). After 12 hours, the reaction was poured into ether (100 ml) and washed with water, brine and dried. Evaporation under reduced pressure and purification by flash column chromatography (30% ethyl acetate-hexane) afforded the title compound as a colorless gum, 250 mg, 55% yield.
$^1$H NMR δ(CDCl$_3$) 7.34-7.25 (m, 10 H), 7.24-7.0 (brs, 5 H), 6.56 (s, 0.5 H), 6.37 (s, 0.5 H), 5.18 (d), 1 H, J=11.5 Hz), 5.07 (m, 2 H), 4.48-4.42 (m, 1H), 4.20-3.98 (m, 4 H), 3.12 (dd, 1 H, J=12.5 and 12.5 Hz), 2.88 (dd, 1 H, J=12.5 and 12.5 Hz), 1.72-1.32 (m, 3 H), 0.92-0.76 (m, 6 H).
MS calcd for (C$_{32}$H$_{36}$N$_2$O$_5$=C$_7$H$_7$)$^+$: 439. Found:439

Example 10
Preparation of 4-(R,S)-Amino-N-[(benzo[b]thiophen-2-ylcarbonyl)-S-leucine]-tetrahydrofuran-3-one Following the procedure of Example 1(e–f) except substituting benzo[b]thiophen-2-ylcarbonyl chloride for piperonyloyl chloride, the title compound was prepared.
$^1$H NMR δ(CDCl$_3$) 8.33 (d, 0.5H, J=6.6Hz), 8.00 (m, 1H), 7.78 (m, 4H), 7.38 (m, 2.5H), 4.87 (m, 1H), 4.63-3.88 (m, 5H), 1.88 (m, 3H), 1.00 (m, 6H).
MS calcd for (C$_{19}$H$_{22}$N$_2$O$_4$S–H)$^+$: 373, Found: 373.

Example 11
Preparation of 4-(R,S)-Amino-N-[(3,4-dimethoxybenzoyl)-S-leucine]-tetrahydrofuran-3-one Following the procedure of Example 1(e–f) except substituting 3,4-dimethoxybenzoyl chloride for piperonyloyl chloride, the title compound was prepared.

$^1$H NMR δ(CDCl$_3$) 7.58 (d, 0.5H, J=6.7Hz), 7.47 (d, 0.5H, J=6.2Hz), 7.33 (m, 2H), 7.04 (d, 0.5H, J=8.0Hz), 6.92 (d, 0.5H, J=8.0Hz), 6.83 (d, 0.5H, J=8.4Hz), 4.77 (m, 1H), 4.53-3.67 (m, 5H), 1.68 (m, 3H), 0.85 (m, 6H).
MS calcd for (C$_{19}$H$_{26}$N$_2$O$_6$–H)$^+$: 377, Found: 377.

Example 12
Preparation of 4-(R,S)-Amino-N-[(indole-6-ylcarbonyl)-S-leucine]-tetrahydrofuran-3-one Following the procedure of Example 1(e–f) except substituting indole-6-ylcarbonyl chloride for piperonyloyl chloride, the title compound was prepared.

$^1$H NMR δ(d$_6$ DMSO) 8.57-7.48 (m, 7H), 6.43 (s, 1H), 4.48-3.55 (m, 6H), 1.80-1.48 (m, 3H), 0.98-0.82 (m, 6H).
MS calcd for (C$_{19}$H$_{23}$N$_3$O$_4$–H)$^+$: 356, Found: 356.

Example 13
Preparation of 4-(R,S)-Amino-N-[(benzofuran-2-ylcarbonyl)-S-leucine]-tetrahydrofuran-3-one Following the procedure of Example 1(e–f) except substituting benzofuran-2-yl-carbonyl chloride for piperonyloyl chloride, the title compound was prepared.

$^1$H NMR δ(CDCl$_3$) 8.00-7.25 (m, 7H), 4.90-4.78 (m, 1H), 4.53-4.48 (m, 1H), 4.38-4.21 (m, 1H), 4.25-3.92 (m, 3H), 1.88 (m, 3H), 1.68 (m, 3H), 0.97 (m, 6H).
MS calcd for (C$_{19}$H$_{22}$N$_2$O$_5$–H)$^+$: 357, Found: 357.

Example 14
Preparation of 4-(R,S)-Amino-N-[(5-aminobenzo[b]thiophen-2-ylcarbonyl)-S-leucine]-tetrahydrofuran-3-one Following the procedure of Example 1(e–f) except substituting 5-aminobenzo[b]thiophen-2-ylcarbonyl chloride for piperonyloyl chloride, the title compound was prepared.

$^1$H NMR δ(CDCl$_3$) 8.00-7.71 (m, 1H), 7.60 (d, 1H, J=3.3 Hz), 7.53 (dd, 1H, J=8.5 and 4.0 Hz), 7.47-6.74 (m, 3H), 4.77 (m, 1H), 4.43 (m, 1H), 4.38-3.50 (m, 4H) 1.77 (m, 3H), 0.85 (m, 6H).
MS calcd for (C$_{19}$H$_{23}$N$_3$O$_4$S+H)$^+$: 390, Found: 390.

Example 15
Preparation of Cyclic Alkoxyketones by Solid Supported Synthesis a) 3-trans-Hydroxy-4-benzyloxycarbonylamino-tetrahydrofuran Benzylchloroformate (20 ml) was added dropwise to a stirred solution of trans-4-amino-3-hydroxytetrahydrofuran (5 g, 20.6 mmol) in dioxane (100 ml) containing 10% aqueous sodium carbonate (200 ml). After 3 hours, the mixture was concentrated to remove the dioxane and then extracted with EtOAc. The combined organic layers were washed with saturated sodium bicarbonate, brine and dried (MgSO$_4$). Evaporation under reduced pressure and purification of the residue by column chromatography afforded the title compound as white crystals, 8.00 g, 70%.

$^1$H NMR δ(CDCl$_3$) 7.35 (s, 5H), 5.30 (s, 2H), 4.91 (br s, 1H), 4.32 (br s, 1H), 4.12-4.00 (m, 3H), 3.71-3.62 (m, 2H), 2.72 (s, 1H).

b) 4-Benzyloxycarbonylamino-tetrahydrofuran-3-one

A solution of bleach (100 ml), containing sodium bicarbonate (7.34 g), was added dropwise to a rapidly stirred mixture of 3-hydroxy-4-benzyloxycarbonylamino-tetrahydrofuran (21 g, 88 mmol), sodium bromide (9.4 g), TEMPO (50 mg) in EtOAc (140 ml), toluene (140 ml) and water (40 ml). After a persistant orange colour developed the mixture was extracted with EtOAc and the combined organic layers were washed with saturated sodium bicarbonate, brine and dried (MgSO$_4$). Evaporation under reduced pressure and purification of the residue by column chromatography afforded the title compound as white crystals, 18 g, 87%.

$^1$H NMR δ(CDCl3) 7.35 (s, 5H), 5.30 (s, 1H), 5.11 (s, 2H), 4.70 (app t, 1 H, J=8.9Hz), 4.36-4.17 (m, 2H), 3.96-3.76 (2H)

c) 3,3-Dimethoxy-4-benzyloxycarbonylamino-tetrahydrofuran

Trimethylorthoformate (29 ml) was added dropwise to a refluxing solution of 4-benzyloxycarbonylamino-tetrahydrofuran-3-one (18 g, 78 mmol) and PTSA (500 mg) in MeOH (100 ml). After 3 hours, the reaction mixture was filtered and concentrated to afford, after column chromatography, the title compound as a yellow oil, 16.2 g, 76%.

$^1$H NMR δ(CDCl$_3$) 7.35 (s, 5H), 5.30 (s, 1H), 5.11 (s, 2H), 4.70 (app t, 1H, J=8.9Hz), 4.36-4.17 (m, 2H), 3.96-3.76 (2H).

d) 3,3-Dimethoxy4-amino-tetrahydrofuran

A mixture of 3,3-Dimethoxy4-benzyloxycarbonylamino-tetrahydrofuran (16 g, 57 mmol) and 10% palladium on charcoal (2 g) in ethanol (200 ml) was stirred under an atmosphere of hydrogen (50 psi) for 12 h. The mixture was filtered and concentrated to afford the title compound as a yellow oil, 8 g, 100%.

$^1$H NMR δ(CDCl$_3$) 7.04 (s, 5H), 4.22-4.04 (m, 5H), 3.83-3.69 (m, 2H), 3.36 (s, 3H), 3.33 (s, 3H).

e) SPS using Ellman Linker

Step A:
Sodium triacetoxyborohydride (10 equiv) was added to a stirred solution of Ellmans resin (ref: C. G. Boojamra, K. M. Burow, L. A. Thompson and J. A. Ellman, *J. Org. Chem.,* 1997, 62, 1240) in DMF containing 1% HOAc. After 5 minutes, the α-amino acid, methyl ester (10 equiv) was added and the mixture was shaken for 1 hour. The resin was then washed with DMF (×7), CH$_2$Cl$_2$ (×7), ether (×2) and dried to a constant weight.

Step B:
NMP was added to a mixture of the above resin, carboxylic acid (10 equiv) and EDC (10 equiv). The mixture was then shaken for 3 hours then washed with DMF (×3), CH$_2$Cl$_2$ (×3), MeOH (×2) and ether (×2). The resin was then resubjected to the above reaction conditions and again washed after 3 hours.

Step C:
Potassium trimethylsilanoate (10 equiv) was added to a shaken mixture of the above resin in THF. After 18 hours, the resin was washed with 5% citric acid in THF (×2), THF (×2), THF-H$_2$O (×2), H$_2$O (×2), THF-H$_2$0 (×2) and finally THF (×2).

Step D:
3,3-Dimethoxy4-amino-tetrahydrofuran (3 equiv) was added to a mixture of the above resin and EDC (3 equiv) in NMP. After 3 hours, the resin was washed with DMF (×7), CH$_2$Cl$_2$ (×7) and ether (×2). The resin was then resubjected to the reaction conditions for a further 3 h, then again washed as above.

Step E: Cleavage
A mixture of 7:2:1 TFA/CH$_2$Cl$_2$/H$_2$O was added to the above resin. After 2 hours, the mixture was filtered and the resin was further washed with CH$_2$Cl$_2$. Removal of the solvent afforded the desired tetrahydrofuran-3-one.

Example 16
Preparation of 4-(R,S)-Amino-N-[(5-chlorobenzofuran-2-ylcarbonyl)-S-leucine]-tetrahydrofuran-3-one Following the general details of Example 15, using the appropriate amino acid methyl ester and carboxylic acid reagents consistent with the final product, the title compound was prepared.

$^1$H NMR δ(CDCl$_3$) 7.62-7.05 (m, 6H), 4.81-4.64 (m, 1H), 4.62-4.54 (m, 1H), 4.43-3.81 (m, 4H), 1.90-1.60 (m, 3H), 1.08-0.81 (m, 6H)

MS calcd for $(C_{19}H_{21}N_2O_5Cl+H)^-$: 393, Found: 393.

Example 17
Preparation of 4-(R,S)-Amino-N-[(5-methoxybenzofuran-2-ylcarbonyl)-S-leucine]-tetrahydrofuran-3-one Following the general details of Example 15, using the appropriate amino acid methyl ester and carboxylic acid reagents consistent with the final product, the title compound was prepared.

$^1$H NMR δ(CDCl$_3$) 7.65-6.84 (m, 6H), 4.83-4.54 (in, 1H), 4.53-4.48 (m, 1H), 4.46-3.68 (m, 4H), 1.90-1.62 (m, 3H), 1.08-0.81 (m, 6H).

MS calcd for $(C_{20}H_{24}N_2O_6+H)^+$: 389, Found: 389.

Example 18
Preparation of 4-(R,S)-Amino-N-[(4-bromobenzoyl)-S-leucine]-tetrahydrofuran-3-one Following the general details of Example 15, using the appropriate amino acid methyl ester and carboxylic acid reagents consistent with the final product, the title compound was prepared.

$^1$H NMR δ(CDCl$_3$) 7.64 (App d, 2H, J=8.5 Hz), 7.60 (App d, 2H, J=8.5 Hz), 4.81-4.67 (m, 1H), 4.62-4.48 (m, 1H), 3.36–4.19 (m, 1H), 4.18-3.78 (m, 3H), 1.81-1.59 (m, 3H), 1.05-0.80 (m, 6H).

MS calcd for $(C_{17}H_{21}N_2O_4Br)^+$: 397, Found: 397.

Example 19
Preparation of 4-(R,S)-Amino-N-[(4-bromobenzoyl)-S-leucine]-tetrahydrofuran-3-one Following the general details of Example 15, using the appropriate amino acid methyl ester and carboxylic acid reagents consistent with the final product, the title compound was prepared.

$^1$H NMR δ(CDCl$_3$) 7.91 (m, 1H), 7.76-7.59 (m, 2H), 7.39-7.18 (m, 1H), 7.04-6.89 (m, 1H), 7.84-6.68 (m, 1H), 4,89-4.4.68 (m, 1H), 4.66-4.56 (m, 1H), 4.27-3.76 (m, 4H), 1.88-1.68 (m, 3H), 1.03-0.78 (m, 6H)

MS calcd for $(C_{17}H_{21}N_2O_4Br)^+$: 397, Found: 397.

Example 20
Preparation of 4-(R,S)-Amino-N-[(5-chlorobenzo[b]thiophen-2-ylcarbonyl)-S-leucine]-tetrahydrofuran-3-one Following the general details of Example 15, using the appropriate amino acid methyl ester and carboxylic acid reagents consistent with the final product, the title compound was prepared.

$^1$H NMR δ(CDCl$_3$) 7.88-7.67 (m, 5H), 7.48-7.38 (m, 1H), 4.81 (br d, 1H, J=6.7Hz), 4.60 (app t, 1H, J=8.8Hz), 4.43-4.30 (m, 1), 4.28-3.84 (m, 3H), 1.86-1.62 (m, 3H), 1.05-0.82 (m, 6H).

MS calcd for $(C_{19}H_{21}N_2O_4SCl-H)^+$: 408, Found: 408.

Example 21
Preparation of 4-(R,S)-Amino-N-[(4-fluorobenzo[b]thiophen-2-ylcarbonyl)-S-leucine]-tetrahydrofuran-3-one Following the general details of Example 15, using the appropriate amino acid methyl ester and carboxylic acid reagents consistent with the final product, the title compound was prepared.

$^1$ H NMR δ(CDCl$_3$) 7.96 (s, 1H), 7.68-7.58 (m, 2H), 7.48-7.32 (m, 1H), 7.06 (dd, 1H, J=9.0 Hz and 9.0 Hz), 4.89-4.72 (m, 1H), 4.65-4.55 (app t, 1H, J=8.8Hz), 4.35 (app q, 1H, J=8.2 Hz), 4.28-3.82 (m, 3H) 1.88-1.62 (m, 3H), 1.05-0.82 (m, 6H).

MS calcd for $(C_{19}H_{21}N_2O_4SF+H)^+$: 393, Found: 393.

Examples 22–66
Preparation of Cyclic Alkoxyketones

By analogous procedures to those described in either Example 1 or Example 15, using the appropriate amino acid and acid or acid chloride reagents consistent with the final products, the compounds of Table 1 were prepared. 1H NMR spectra and/or mass spectra were consistent with the structures in Table 1.

TABLE 1

| Example | R$^3$ | R" | synthesis method |
|---|---|---|---|
| 22 |  | 3,4-difluorophenyl | soln |
| 23 |  | 4-benzylpiperidin-1-yl | soln |
| 24 |  | 4-benzylpiperazin-1-yl | soln |
| 25 |  | 4-(3,4-methylenedioxybenzyl)piperazin-1-yl | soln |
| 26 |  | 4-(tertbutoxycarbonyl)piperazin-1-yl | soln |
| 27 |  | piperazin-1-yl | soln |

TABLE 1-continued

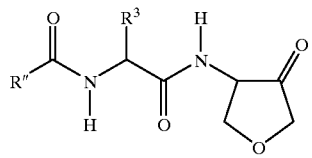

| Example | R³ | R" | synthesis method |
|---|---|---|---|
| 28 | isobutyl | benzimidazol-5-yl | soln |
| 29 | isobutyl | 6-quinolyl | soln |
| 30 | isobutyl | 5-indolyl | soln |
| 31 | isobutyl | 2-naphthyl | soln |
| 32 | isobutyl | 2-pyridyl | soln |
| 33 | isobutyl | 4-benzyloxyphenyl | soln |
| 34 | isobutyl | 3-benzyloxyphenyl | soln |
| 35 | isobutyl | 4-hydroxyphenyl | soln |
| 36 | isobutyl | 5-nitrobenzo[b]thiophen-2-yl | soln |

TABLE 1-continued

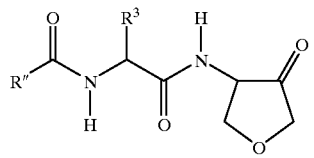

| Example | R³ | R" | synthesis method |
|---|---|---|---|
| 37 | isobutyl | 2-(thien-2-yl)ethen-1-yl | soln |
| 38 | isobutyl | 4-methoxyphenyl | SPS |
| 39 | isobutyl | 3-methoxyphenyl | SPS |
| 40 | isobutyl | 7-ethoxybenzofuran-1-yl | SPS |
| 41 | isobutyl | 5-nitrobenzofuran-1-yl | SPS |
| 42 | isobutyl | 4-(2-methoxyphenyl)phenyl | SPS |
| 43 | isobutyl | 3-(2-methoxyphenyl)phenyl | SPS |
| 44 | isobutyl | 4-cyanophenyl | SPS |
| 45 | isobutyl | 3-nitrophenyl | SPS |

TABLE 1-continued

[Structure: R''-C(=O)-NH-CR³H-C(=O)-NH-[3-oxotetrahydrofuran-3-yl]]

| Example | R³ | R" | synthesis method |
|---|---|---|---|
| 46 | isobutyl | 3-(dimethylaminoethyl)-4-methoxyphenyl | SPS |
| 47 | isobutyl | 2-(2-chlorophenyl)ethen-1-yl | SPS |
| 48 | isobutyl | 4-trifluoromethoxyphenyl | SPS |
| 49 | isobutyl | 4-methanesulphonylphenyl | SPS |
| 50 | isobutyl | 4-iodophenyl | SPS |
| 51 | isobutyl | 4-chlorobenz[b]thiophen-2-yl | SPS |
| 52 | isobutyl | 5,6-dimethoxybenzo[b]thiophen-2-yl | SPS |
| 53 | isobutyl | 5,6-methylenedioxybenzo[b]thiophen-2-yl | SPS |
| 54 | isobutyl | 7-chlorobenzo[b]thiophen-2-yl | SPS |
| 55 | PhCH₂ | benzo[b]thiophen-2-yl | SPS |
| 56 | PhCH₂ | 2-thienyl | SPS |
| 57 | PhCH₂ | 3,4-dimethoxyphenyl | SPS |
| 58 | PhCH₂ | 4-bromophenyl | SPS |
| 59 | PhCH₂ | quinolin-2-yl | SPS |
| 60 | isobutyl | 2-thienyl | SPS |
| 61 | isobutyl | CH₃ | SPS |
| 62 | cyclohexylmethyl | benzo[b]thiophen-2-yl | SPS |
| 63 | cyclohexylmethyl | 2-thienyl | SPS |
| 64 | cyclohexylmethyl | 3,4-dimethoxyphenyl | SPS |

TABLE 1-continued

| Example | R³ | R" | synthesis method |
|---|---|---|---|
| 65 | cyclohexylmethyl | 4-bromophenyl | SPS |
| 66 | cyclohexylmethyl | quinolin-2-yl | SPS |

Example 67

Preparation of 4-(R,S)-Amino-N-[(benzyloxycarbonyl)-S-leucine]-tetrahydropyran-3-one a) trans-4-amino-3-hydroxytetrahydropyran hydrochloride Following the procedures of Examples 1(a) and 1(b), substituting 3,4-epoxytetrahydropyran for 3,4-epoxytetrahydrofuran, the title compound was prepared.

b) trans-4-(R,S)-amino-N-[(benzyloxycarbonyl)-S-leucine]-3-hydroxytetrahydropyran Pivaloyl chloride (5.28 ml, 43 mmol) was added to a solution of N-carbobenzyloxy-L-leucine (12.48 g, 47 mmol) in dichloromethane (300 ml). After 1 hour, a mixture of trans-4-amino-3-hydroxytetrahydropyran hydrochloride (6 g, 39 mmol) and triethylamine (10.8 ml, 79 mmol) in dichloromethane (100 ml) was added and the mixture allowed to stir overnight. The reaction mixture as washed with 1N HCl, saturated sodium hydrogen carbonate and dried. Evaporation under reduced pressure afforded a pale oil. Purification by chromatography (ethyl acetate/hexane eluant) gave the trans-4-(R,S)-amino-N-[(benzyloxycarbonyl)-S-leucine]-3-hydroxytetrahydropyran as a white paste, 5.5 g, 39% yield:
$^1$H NMR δ(CDCl$_3$) 7.35 (s, 5H), 5.0 (m, 3H), 4.16-3.89 (m, 4H), 3.44-3.36 (m, 2H), 3.13 (t, 1H), 1.84-1.53 (m, 2H), 1.28-1.22 (m, 3H), 0.93 (m, 6H).

c) 4-(R,S)-amino-N-[(benzyloxycarbonyl)-S-leucine]tetrahydropyran-3-one

Following the procedure of Example 1(f), except substituting 4-(R,S)-amino-N-[(benzyloxycarbonyl)-S-leucine]-3-hydroxytetrahydropyran for 4-(R,S)-amino-N-[(3,4-methylenedioxybenzoyl)-S-leucine]-3-hydroxytetrahydrofuran, the title compound was prepared:
$^1$H NMR δ(d$_6$ DMSO) 8.15 (d, 1H), 7.39-7.29 (m, 5H), 5.02 (d, 2H), 4.63 (m, 1H), 4.14-4.10 (m, 2H), 3.97-3.83 (m, 3H), 2.10 (m, 1H), 1.92 (m, 1H). 1.61 (m, 1H), 1.45 (m, 1H), 0.95 (m, 6H).
MS calcd for (C$_{19}$H$_{26}$N$_2$O$_5$+H)$^+$: 363. Found 363.

Example 68

Preparation of 4-(R,S)-Amino-N-[(benzo[b]thiophen-2-ylcarbonyl)-S-leucine]-tetrahydropyran-3-one a) trans-4-(R,S)-Amino-N-(S-leucine)-3-hydroxytetrahydropyran hydrochloride A mixture of 4-(R,S)-amino-N-[(benzyloxycarbonyl-S-leucine]-3-hydroxytetrahydropyran (2.8 g, 7.75 mmol) and 10% palladium on charcoal (300 mg) in ethanol (100 ml) was stirred under an atmosphere of hydrogen (50 psi) for 12 hours. The mixture was filtered and treated with ethereal HCl to afford, after evaporation under reduced pressure, the title compound as a brown solid, 1.40 g, 68% yield:
$^1$H NMR δ(CDCl$_3$) 8.30 (m, 2H), 8.02 (m, 1H), 4.06-3.92 (m, 4H), 3.50-3.35 (m, 2H), 3.12 (t, 1H), 1.89-1.54 (m, 2H), 1.23 (m, 3H), 0.93 (m, 6H).

b) trans-4-(R,S)-amino-N-[(benzothiophene-2-carbonyl)-S-leucine]-3-hydroxytetrahydropyran Benzothiophene-2-carbonyl chloride (442 mg, 2.25 mmol) was added to a solution of trans-4-(R,S)-amino-N-(S-leucine)-3-hydroxytetrahydropyran (133 mg, 0.5 mmol) in dioxan (7 ml) and saturated sodium hydrogen carbonate (7 ml). After 30 min, the reaction mixture was diluted with ethyl acetate, the organic layer washed with saturated sodium hydrogen carbonate, dried and evaporated under reduced pressure to give a white solid. Purification by chromatography (ethyl acetate/hexane eluant) gave the trans-4-(R,S)-amino-N-[(benzothiophene-2-carbonyl)-S-leucine]-3-hydroxytetrahydropyran as a white solid, 160 mg, 84%.

c) 4-(R,S)-Amino-N-[(benzothiophene-2-carbonyl)-S-leucine]-tetrahydropyran-3-one Following the procedure of Example 1(f) except substituting trans-4-(R,S)-amino-N-[(benzothiophene-2-carbonyl)-S-leucine]-3-hydroxytetrahydropyran for 4-(R,S)-amino-N-[(3,4-methylenedioxybenzoyl)-S-leucine]-3-hydroxytetrahydrofuran, the title compound was prepared:
$^1$H NMR δ(CDCl$_3$) 7.84-7.76 (m, 2H), 7.41 (m, 2H), 7.05 (m, 1H), 4.83-4.61 (m, 2H), 4.18-3.77 (m, 4H), 2.73-2.53 (m, 1H), 1.98-1.75 (m. 2H), 1.26 (m, 3H), 0.92 (m, 6H).
MS calcd for (C$_{20}$H$_{24}$N$_2$O$_4$S+H)$^+$: 389. Found 389.

Example 69

Preparation of 4-(R,S)-Amino-N-[(4-phenoxybenzoyl)-S-leucine]-tetrahydrofuran-3-one By analogous methods to those detailed in Example 15, the title compound was prepared.
$^1$H NMR δ(CDCl$_3$, 250 MHz) 7.74 (d, 2 H, J=10.9 Hz), 7.37 (dd, 2 H, J=7.7 and 7.7 Hz), 7.20 (dd, 1 H, J=7.5 and 7.5 Hz), 7.03 (d, 2 H, J=7.7 Hz), 7.0 (d, 2 H, J=7.7 Hz), 6.98-6.82 (m, 2 H), 4.83-4.68 (m, 1H), 4.66-4.45 (m, 1H), 4.34-3.70 (m, 4 H), 1.98-1.54 (m, 3 H), 1.08-0.78 (m, 6 H).
MS calcd for (C$_{23}$H$_{26}$N$_2$O$_5$-H)$^+$: 409 Found: 409.

Example 70

Preparation of 4-(R,S)-Amino-N-[(4-phenylbenzoyl)-S-leucine]-tetrahydrofuran-3-one By analogous methods to those detailed in Example 15, the title compound was prepared.
$^1$H NMR δ(CDCl$_3$, 250 MHz) 7.83 (d, 2 H, I =8.2 Hz), 7.70-50 (m, 4 H), 7.48-32 (m, 4 H), 7.30-7.12 (m, 1 H), 6.88-6.72 (m, 1H), 4.88-4.70 (m, 1 H), 4.65-52 (m, 1H), 4.38-3.78 (m, 4 H), 1.92-1.60 (m, 3 H), 1.08-0.78 (m, 6 H).
MS calcd for (C$_{23}$H$_{26}$N$_2$O$_4$-H)$^+$: 393. Found: 393.

Example 71
Preparation of 4-(R,S)-Amino-N-[(6-trifluoromethylbenzo[b]thiophen-2-ylcarbonyl)-S-leucine]-tetrahydrofuran-3-one By analogous methods to those detailed in Example 15, the title compound was prepared.
$^1$H NMR δ(DMSO, $d_6$, 250 MHz) 8.82 (d, 1 H, J=6.0 Hz), 8.43 (s, 1H), 8.48-8.44 (m, 0.5 H), 8.34 (d, 0.5 H, J=7.8 Hz), 8.23 (s, 1 H), 8.04 (d, 1 H, J=8.4 Hz), 7.60 (dd, 1 H, J=1.5 and 8.5 Hz), 4.49-4.38 (m, 1 H), 4.26-3.68 (m, 5 H), 1.70-1.36 (m, 3 H), 0.80 (d, 3 H, J=6 Hz), 0.76 (d, 3 H, J=6.0 Hz)
MS calcd for $(C_{20}H_{21}F_3N_2O_4S-H)^+$: 443. Found: 443.

Example 72
Preparation of 4-(R,S)-Amino-N-[(4-ethyllbenzoyl)-S-leucine]-tetrahydrofuran-3-one By analogous methods to those detailed in Example 15, the title compound was prepared.
$^1$H NMR δ(CDCl$_3$, 250 MHz) 7.76 (d, 2 H, J=8.0 Hz), 7.62-7.42 (m, 1H), 7.22 (d. 2 H, J=7.8 Hz), 7.04-6.80 (m, 1 H), 4.91-4.73 (m, 1H), 4.61-4.45 (m, 1H), 4.36-3.72 (m, 4 H), 2.68 (q, 2 H, J=7.6 Hz), 1.88-1.58 (m, 3 H), 1.23 (t, 3 H. J=7.6 Hz), 0.98-0.88 (m, 6H)
MS calcd for $(C_{19}H_{26}N_2O_4-H)^+$: 345 Found: 345.

Example 73
Preparation of 4-(R,S)-Amino-N-[(4-(tert-butyl)benzoyl)-S-leucine]-tetrahydrofuran-3-one By analogous methods to those detailed in Example 15, the title compound was prepared.
$^1$H NMR δCDCl$_3$, 250 MHz) 7.76 (brd, 2 H, J=7.5 Hz), 7.46 (brd, 2 H, J 7.5 Hz), 6.92-6.76 (m, 2H), 4.88-4.68 (m, 1H), 4.58-4.43 (m, 1H), 4.37-3.71 (m, 4 H), 1.82-1.57 (m, 3 H), 1.32 (s, 9 H), 1.00-0.82 (m, 6 H).
MS calcd for $(C_{21}H_{30}N_2O_4+H)^+$: 375. Found: 375.

Example 74
Preparation of 4-(R,S)-Amino-N-[(5-methoxybenzo[b]thiophen-2-ylcarbonyl)-S-leucine]-tetrahydrofuran-3-one By analogous methods to those detailed in Example 15, the title compound was prepared.
$^1$H NMR δ(CDCl$_3$, 250MHz) 7.84-7.54 (m, 2 H), 7.20 (d, 1 H. J=2.0Hz), 7.10 (d, 1 H, J=2.3 Hz), 7.06 (d, 1 H, J=2.3 Hz), 6.78 (d, 1 H, J=8.1 Hz), 4.82-4.68 (m, 1 H), 4.59 (appt, 1 H, J=8.8 Hz), 4.49-3.61 (m, 4 H), 3.84 (s, 3 H), 1.82-1.58 (m, 3 H), 1.08-0.72 (m,6H).
MS calcd for $(C_{20}H_{24}N_2O_5S-H)^+$: 403. Found: 403.

Example 75
Preparation of 4-(R,S)-Amino-N-[(4-nitrobenzo[b]thiophen-2-ylcarbonyl)-S-leucine]-tetrahydrofuran-3-one By analogous methods to those detailed in Example 15, the title compound was prepared.
$^1$H NMR δ(CDCl$_3$, 250 MHz) 8.31 (s, 1 H), 7.96 (d, 1 H, J=7.2 Hz), 7.62-7.18 (m, 4 H), 4.84 (appd, 1 H, J=7.5 Hz), 4.70-3.72 (m, 5 H), 1.94-1.60 (m, 3 H), 1.11-0.80 (m, 6 H).
MS calcd for $(C_{19}H_{21}N_3O_4S-NO_2)^+$: 373. Found: 373.

Example 76
Preparation of 4-(R,S)-Amino-N-[(6-bromobenzo[b]thiophen-2-ylcarbonyl)-S-leucine]-tetrahydrofuran-3-one By analogous methods to those detailed in Example 15, the title compound was prepared.
$^1$H NMR δ(CDCl$_3$, 250 MHz) 8.03 (s, 1H), 7.81-7.58 (m, 2 H), 7.54-7.40 (m, 1 H), 7.22-6.98 (m, 2 H), 4.74 (appd, 1 H, J=7.5 Hz), 4.59 (appq, 1 H, J=7.5 and 14.0 Hz), 4.48-3.74 (m, 4 H), 1.85-1.58 (m, 3 H), 1.10-0.78 (m, 6 H).
MS calcd for $(C_{19}H_{21}BrN_2O_1S-H)^+$: 452. Found: 452.

Example 77
Preparation of 4-(R,S)-Amino-N-[(5-bromobenzo[b]thiophen-2-ylcarbonyl)-S-leucine]-tetrahydrofuran-3-one By analogous methods to those detailed in Example 15, the title compound was prepared.
$^1$H NMR δ(CDCl$_3$, 250 MHz) 8.04-7.90 (m, 1 H), 7.88-7.18 (m,5 H), 4.88-4.68 (m, 1 H), 4.68-4.52 (m, 1H), 4.46-3.88 (m, 4 H), 1.92-1.52 (m, 3 H), 1.08-0.80 (m, 6 H).
MS calcd for $(C_{19}H_{21}BrN_2O_4S-H)^+$: 452. Found: 452.

Example 78
Preparation of 4-(R,S)-Amino-N-[(6-methoxybenzo[b]thiophen-2-ylcarbonyl)-S-leucine]-tetrahydrofuran-3-one By analogous methods to those detailed in Example 15, the title compound was prepared.
$^1$H NMR δ(CDCl$_3$, 250 MHz) 7.79-7.61 (m, 2 H), 7.32-7.14 (m, 2 H), 7.00 (dd, 1 H, J=1.5 and 8.8 Hz), 6.89-6.67 (m, 1H), 4.75 (appq, 1 H, J=8.2 and 16.2 Hz), 4.57 (appt, 1 H, J=8.6 and 17.4 Hz), 4.49-3.71 (m,4 H), 3.85 (s, 3 H), 1.92-1 52 (m, 3 H), 1.08-0.78 (m, 6 H).
MS calcd for $(C_{20}H_{24}N_2O_5S-H)^+$: 403. Found: 403.

Examples 79–93

By analogous procedures to those described in Example 15, using the appropriate amino acid and acid or acid chloride reagents consistent with the final products, the compounds of Table 2 were also prepared. 1H NMR spectra and/or mass spectra were consistent with the structures in Table 2.

TABLE 2

![structure]

| Example | R$^3$ | R" | synthesis method |
|---|---|---|---|
| 79 |  | phenyl | SPS |
| 80 |  | 3-chlorophenyl | SPS |
| 81 |  | 2-phenylethen-1-yl | SPS |
| 82 |  | 3-fluorophenyl | SPS |

TABLE 2-continued

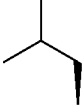

| Example | R³ | R" | synthesis method |
|---|---|---|---|
| 83 | 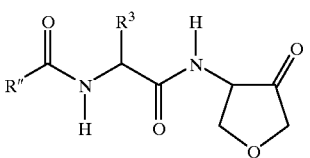 | 3-hydroxyphenyl | SPS |
| 84 | 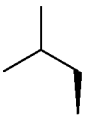 | 4-methylphenyl | SPS |
| 85 | 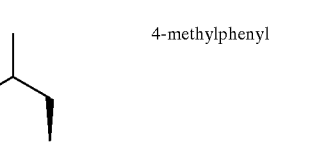 | 4-isopropylphenyl | SPS |
| 86 |  | 4-trifluoromethylpheny | SPS |
| 87 | 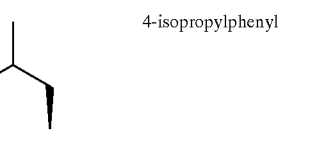 | 4-methylthiophenyl | SPS |
| 88 |  | 4-(benzylsulphonylmaino)phenyl | SPS |
| 89 | 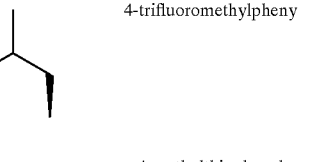 | 4-(diethylaminosulphonyl)phenyl | SPS |
| 90 |  | 4-(acetylamino)phenyl | SPS |
| 91 | 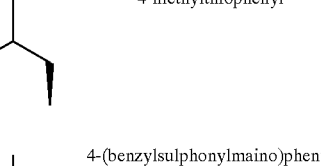 | 4-benzoylphenyl | SPS |

TABLE 2-continued

| Example | R³ | R" | synthesis method |
|---|---|---|---|
| 92 | 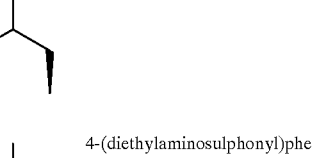 | 4-acetylphenyl | SPS |
| 93 |  | 4-(4-oxopent-1-yl)phenyl | SPS |

Example 94
Preparation of 4-S-Amino-N-[(benzo[b]thiophen-2-ylcarbonyl)-S-leucine]-tetrahydrofuran-3-one
(a) trans-4-S-Amino-3-R-hydroxytetrahydrofuran hydrochloride A mixture of trans-4-S-azido-3-R-hydroxytetrahydrofuran (ref L. E. Martinez, J. L. Leighton, D. E. Carsten and E. N. Jacobsen, *J. Amer Chem. Soc.* 1995, 117, 5897) (10 g, 77 mmol) and 10% palladium on charcoal (1 g) in ethanol (150 ml) was stirred under an atmosphere of hydrogen (50 psi) for 12 h. The mixture was filtered and treated with 100 ml of ethanolic HCl to afford, after evaporation under reduced pressure, the title compound as a brown solid. 10.5 g, 97% yield. m.p. 132° C.
¹H NMR δ(D₂O) 4.54-4.52 (m, 1H), 4.24-4.13 (m, 2 H), 3.98-3.61 (m, 3 H).
(b) trans-4-S-Amino-N-[(benzyloxycarbonyl)-S-leucine]-3-R-hydroxytetrahydrofuran Trimethylacetyl chloride (5.4 ml, 44 mmol) was added to a stirred solution of N-Cbz-L-leucine (12.7 g, 48 mmol) and triethylamine (14 ml, 52 mmol) in THF (200 ml). After 1 h, trans-4-S-amino-3-R-hydroxytetrahydrofuran.HCl (5.58 g, 40 mmol) was added and the mixture was allowed to stir at reflux for 16 h. The reaction mixture was filtered and evaporated under reduced pressure. Flash column chromatography (80% ethyl acetate-hexane) afforded the title compound as a white foam, 10.6 g, 76% yield.
¹H NMR δ(CDCl₃) 7.76 (d, 1 H, J=5.3 Hz), 7.33-7.20 (m, 5 H), 6.43 (d, 1 H, J=8.9 Hz), 5.01 (appd, 2 H, J=3.0 Hz), 4 60-3.65 (m, 6 H), 1.61-1.42 (m, 3 H), 0.93- 0.88 (m, 6H)
(c) trans-4-S-Amino-N-(S-leucine)-3-R-hydroxytetrahydrofuran hydrochloride A mixture of trans-4-S-Amino-N-[(carbobenzyloxy)-S-leucine]-3-R-hydroxytetrahydrofuran (2.0 g, 5.7 mmol and 10% palladium on charcoal (500 mg) in ethanol (100 ml) was stirred under an atmosphere of hydrogen (50 psi) for 12 hours. The reaction mixture was then filtered diluted with ethereal HCl (100 ml, 1 molar) and evaporated under reduced pressure to afford the title compound as a white foam, 1.5 g, 100% yield.
¹H NMR δ(D₂O) 4.20-4.05 (m, 2 H), 4.06-4.00 (m, 1 H), 3.90-3.83 (m, 2 H), 3.68-3.52 (m, 2 H), 1.65-1.47 (m, 3 H), 0.86-0.78 (m, 6 H).

(d) trans-4-S-Amino-N-[(2-benzo(b)thiophenecarbonyl)-S-leucine-3-R-hydroxytetrahydrofuran N,N-Diisopropylethylamine (0.4 ml, 2.0 mmol) was added to a stirred solution of trans-4-S-amino-N-(S-leucine)-3-R-hydroxytetrahydrofuran.HCl salt (380 mg, 1.1 mmol) in dichloromethane (10 ml). After 5 minutes benzo[b]thiophene-2-carbonyl chloride (196 mg, 1.0 mmol) was added and the mixture was allowed to stir for 1 h then evaporated under reduced pressure. Flash column chromatography (40% acetone-hexane) afforded the title compound as a white foam, 271 mg, 75% yield.
$^1$H NMR $\delta(d_6$ DMSO, 400 MHz) 8.72 (d, 1 H, J=8.5 Hz), 8.25 (s, 1H), 8.04 (d, 1 H, J=8.5 Hz), 7.95 (d, 1 H, J=8.5 Hz), 7.46-7.43 (m ,2 H), 5.23 (d, 1 H, J=3.94 Hz), 4.54-4.47 (m, 1H), 4.03-4.00 (m, 2 H), 3.90 (dd, 1 H, J=5.4 and 8.9 Hz), 3.82 (dd, 1 H, J=4.4 and 9.3 Hz). 3.53- 3.48 (m, 2 H), 1.72-1.66 (m, 2 H), 1.52-1.48 (m, 1H), 0.91 (d, 3 H, J=6.4 Hz), 0.88 (d, 3 H, J=6.4 Hz).
MS calcd for $(C_{18}H_{24}N_2O_5+H)^+$: 365. Found: 365.
(e) 4-S-Amino-N-[(2-benzo(b)thiophenecarbonyl)-S-leucine]-tetrahydrofuran-3-one Dess-Martin periodinane (200 mg, 0.5 mmol) was added to a stirred solution of trans-4-S-Amino-N-[(2-benzo(b)thiophenecarbonyl)-S-leucine-3-R-hydroxytetrahydrofuran (150 mg, 0.40 mmol) in dichloromethane (10 ml). After 1 h, ether (20 ml) was added followed by sodium thiosulfate (1 g). After an additional 15 mins the reaction was washed with saturated sodium hydrogen carbonate, brine and dried. Evaporation of the solvent gave the title compound as a white foam, 147 mg, 100% yield.
$^1$H NMR $\delta(d_6$ DMSO, 400 MHz) 8.82 (d, 1 H, J=4.0 Hz), 8.46 (d, 1 H, J=4.0 Hz), 8.28 (s, 1H), 8.05 (d, 1 H, J=4.0 Hz), 7.98 (d, 1 H, I =4.0 Hz), 7.47-7.44 (m, 2 H), 4.54-4.51 (m, 1H), 4.33-4.18 (m, 3 H), 4.08-3.80 (m, 3 H), 1.74-1.67 (m, 2 H), 1.58-1.56 (m, 1H), 0.92 (d, 3 H, J=6.4 Hz), 0.88 (d, 3 H, J=6.4 Hz).
MS calcd for $(C_{19}H_{22}N_2O_4-H)^+$: 373. Found: 373.

Example 95
Preparation of 4-R-Amino-N-[(2-benzo(b)thiophenecarbonyl)-S-leucine]-tetrahydrofuran-3-one Following the procedures of Example 94(a-e), but starting instead with trans-4-R-azido-3-S-hydroxytetrahydrofuran (ref L. E. Martinez, J. L. Leighton, D. E. Carsten and E. N. Jacobsen, *J. Amer Chem. Soc*, 1995, 117, 5897) in the method of Example 94(a), the title compound was prepared.
$^1$H NMR $\delta(d_6$ DMSO, 400 MHz) 8.82 (d, 1 H, J=4.0 Hz), 8.52 (d, 1 H, J=4.0 Hz), 8.28 (s, 1H), 8.01 (d, 1 H, J=4.0 Hz), 7.95 (d, 1 H, J=4.0 Hz), 7.47-7.44 (m, 2 H), 4.54-4.51 (m, 1H), 4.33-4.18 (m, 3 H), 4.33 (appt, 1 H, J=8.5 Hz). 4.22 (dd, 1 H, J=8.7 and 16.0 Hz), 4.07 (appd. 1 H, J=16.6 Hz), 3.90 (appd, 1 H, J=16.6 Hz), 3.81 (appt, 1 H, J=8.5 Hz), 1.74-1.67 (m, 2 H), 1.58-1.56 (m, 1H), 0.92 (d, 3 H, J=6.4 Hz), 0.88 (d, 3 H, J=6.4 Hz).
MS calcd for $(C_{19}H_{22}N_2O_4-H)^+$: 373. Found: 373.

Example 96
Preparation of 4-S-Amino-N-[(2-napthol)-S-leucine]-tetrahydrofuran-3-one Following the procedures of Example 94, using the appropriate carboxylic acid chloride and the 4-azido-3-hydroxytetrahydrofuran of the required stereochemistry to be consistent with the final product, the following compound was prepared.
$^1$H NMR $\delta(d_6$ DMSO, 400 MHz) 8.64 (d, 1 H, J=3.8 Hz), 8.54 (s, 1H), 8.42 (d, 1 H, J=3.8 Hz), 8.03 (d, 1 H, J=3.8 Hz), 8.02-7.95 (in, 3 H), 7.62-7.58 (m, 2 H), 4.63-4.60 (m, 1 H), 4.35-4.27 (m, 2 H), 4.08 (appd, 1 H, J=16.8 Hz), 3.86 (appd, 1 H, J=16.8 Hz), 3.82 (appt, 1 H, J=8.0 Hz), 1.75-1.64 (m, 2 H), 1.62-1.55 (m, 1H), 0.92 (d, 3 H, J=6.0 Hz), 0.88 (d. 3 H, J=6.0 Hz).
MS calcd for $(C_{21}H_{24}N_2O_4-H)^+$: 367. Found: 367.

Example 97
Preparation of 4R-N-[(2-napthoyl)-S-leucine]-tetrahydrofuran-3-one

Following the procedures of Example 94, using the appropriate carboxylic acid chloride and the 4-azido-3-hydroxytetrahydrofuran of the required stereochemistry to be consistent with the final product, the following compound was prepared.
$^1$H NMR $\delta(d_6$ DMSO, 400 MHz) 8.62 (d, 1 H, J=3.8 Hz), 8.52 (s, 1H), 8.50 (d, 1 H, J=3.8 Hz), 8.04 (d, 1 H, J=3.8 Hz), 8.02-7.95 (in, 3 H), 7.62-7.58 (m, 2 H), 4.63-4.60 (m, 1H), 4.32 (appt, 1 H, J=8.8 Hz), 4.23 (ddd, 1 H, J=8.8 and 16.0 Hz), 4.04 (appd, 1 H, J=16.4 Hz), 3.86 (appd, 1 H, J=16.4 Hz), 3.81 (appt, 1 H, J=8.0 Hz), 1.75-1.64 (m, 2 H), 1.62-1.55 (m, 1H), 0.92 (d, 3 H, J=6.0 Hz), 0.88 (d, 3 H, J=6.0 Hz).
MS calcd for $(C_{21}H_{24}N_2O_4-H)^+$: 367. Found: 367.

Example 98
Preparation of 4-S-Amino-N-[(quinoline-2-carbonyl)-S-leucine]-tetrahydrofuran-3-one Following the procedures of Example 94, using the appropriate carboxylic acid chloride and the 4-azido-3-hydroxytetrahydrofuran of the required stereochemistry to be consistent with the final product, the following compound was prepared.
$^1$H NMR $\delta(d_6$ DMSO, 400 MHz) 8.80 (d, 1 H, J=9.0 Hz), 8.70 (d, 1 H, J=6.9 Hz), 8.63 (d, 1 H, J=8.5 Hz), 8.39 (d, 1 H, J=2.5 Hz), 8.27 (d, 1 H, J=2.5 Hz), 8.21 (d, 1 H, J=7.9 Hz), 7.95 (appt, 1 H, J=8.2 Hz), 7.77 (appt, 1 H, J=7.1 Hz), 4.75-4.66 (m, 1 H), 4.41-4.26 (m, 2 H), 4.16-3.79 (m, 3 H), 1.82-1.63 (11, 3 H), 0.97-0.88 (m, 6 H).
MS calcd for $(C_{20}H_{23}N_3O_4+H)^+$: 370. Found: 370.

Example 99
Preparation of 4-R-Amino-N-[(quinoline-2-carbonyl)-S-leucine]-tetrahydrofuran-3-one Following the procedures of Example 94, using the appropriate carboxylic acid chloride and the 4-azido-3-hydroxytetrahydrofuran of the required stereochemistry to be consistent with the final product, the following compound was prepared.
$^1$H NMR $\delta(d_6$ DMSO, 400 MHz) 8.88 (d, 1 H, J=9.0 Hz), 8.82 (d, 1 H, J=6.7 Hz), 8.70 (d, 1 H, J=8.5 Hz), 8.30 (d, 1 H, J=2.5 Hz), 8.27 (d, 1 H, J=2.5 Hz), 8.21 (d, 1 H, J=7.9 Hz), 8.02 (appt, 1 H, J=7.0 Hz), 7.87 (appt, 1 H, J=7.0 Hz), 4.82-4.73 (m, 1 H), 4.48-3.88 (m, 5 H), 1.88-1.70 (m, 3 H), 1.05-1.02 (m, 6 H).
MS calcd for $(C_{21}H_{23}N_3O_4+H)^+$: 370. Found: 370.

Example 100
Preparation of 4-S-Amino-N-[(5-methoxybenzofuran-2-ylcarbonyl)-S-leucine]-tetrahydrofuran-3-one Following the procedures of Example 94, using the appropriate carboxylic acid chloride and the 4-azido-3-hydroxytetrahydrofuran of the required stereochemistry to be consistent with the final product, the following compound was prepared.
$^1$H NMR $\delta(d_6$ DMSO, 400 MHz) 8.73 (d, 1 H, J=8.4 Hz), 8.52 (d, 1 H, J=7.0 Hz), 7.65-7.62 (m, 2 H), 7.33 (d, 1 H, J=2.6 Hz), 7.12 (dd, 1 H, J=2.6 and 9.2 Hz), 4.64-4.55 (m, 1 H), 4.42-4.30 (m, 2 H), 4.18-3.87 (m, 3 H), 3.86 (s, 3 H), 1.84-1.57 (m, 3 H), 0.98-0.87 (m, 6 H).
MS calcd for $(C_{20}H_{24}N_2O_6+H)^+$: 389. Found: 389.

Examples 101–108

By analogous procedures to those described in Example 15, using the appropriate amino acid and acid or acid chloride reagents consistent with the final products, the compounds of Table 3 were also prepared. $^1$H NMR spectra and/or mass spectra were consistent with the structures in Table 3.

TABLE 3

| Example | R³ | R″ | synthesis method |
|---|---|---|---|
| 101 | isobutyl | 6-hydroxybenzo[b]thiophen-2-yl | SPS |
| 102 | isobutyl | 5-hydroxybenzo[b]thiophen-2-yl | SPS |
| 103 | isobutyl | 4-(3-(hydroxymethyl)phenyl)phenyl | SPS |
| 104 | isobutyl | 3-phenylphenyl | SPS |
| 105 | isobutyl | 4-(3-oxophenyl)phenyl | SPS |
| 106 | isobutyl | 4-(3-(aminosulphonyl)phenyl)phenyl | SPS |
| 107 | isopropyl | benzo[b]thiophen-2-yl | SPS |
| 108 | n-butyl | benzo[b]thiophen-2-yl | SPS |

Examples 109–126

Following the procedures of Example 94, using the appropriate carboxylic acid chloride and the 4-azido-3-hydroxytetrahydrofuran of the required stereochemistry to be consistent with the final products, examples 109–126 were prepared. $^1$H NMR spectra and/or mass spectra were consistent with the structures in Table 4.

TABLE 4

| Example | R³ | R″ | stereochem at 4-position |
|---|---|---|---|
| 109 | isobutyl | 4-(pyrid-3-yl)phenyl | S |
| 110 | isobutyl | 4-(pyrid-2-yl)phenyl | S |
| 111 | isobutyl | 4-acetylphenyl | S |
| 112 | isobutyl | benzyloxy | S |
| 113 | isobutyl | 3,4-dimethoxyphenyl | S |
| 114 | isobutyl | benzofuran-2-yl | S |
| 115 | isobutyl | 4-(6-methylpyrid-3-yl)phenyl | S |
| 116 | isobutyl | 5-chlorobenzo[b]thiophen-2-yl | S |

TABLE 4-continued

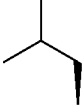

| Example | R³ | R" | stereochem at 4-position |
|---|---|---|---|
| 117 | 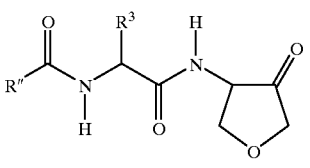 | 4-(pyrid-4-yl)phenyl | S |
| 118 | 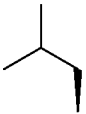 | 2-chlorophenyl | S |
| 119 | 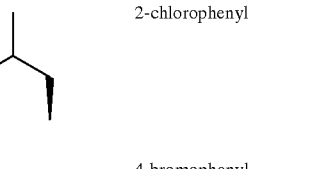 | 4-bromophenyl | S |
| 120 |  | 4-chlorobenzo[b]thiophen-2-yl | S |
| 121 | 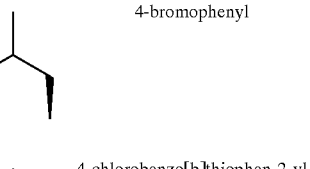 | 4-benzylpiperidin-1-yl | S |
| 122 |  | 3,4-dichlorophenyl | S |
| 123 | 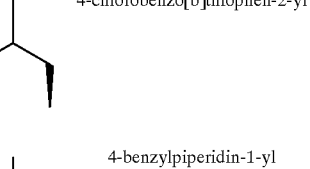 | 3,4-dimethoxyphenyl | R |
| 124 |  | benzofuran-2-yl | R |
| 125 | 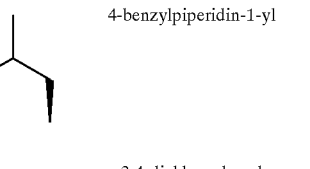 | 3-chlorophenyl | S |

TABLE 4-continued

| Example | R³ | R" | stereochem at 4-position |
|---|---|---|---|
| 126 | 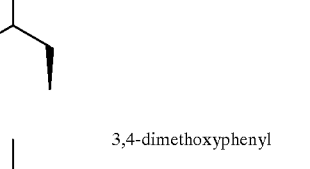 | 5-chlorobenzo[b]thiophen-2-yl | R |

Examples 127–129

Using the SPS procedure of Example 15 but substituting 3,3-dimethoxy-4-aminotetrahydropyran for 3,3-dimethoxy 4-aminotetrahydrofuran, and using appropriate amino acid and carboxylic acid reagents consistent with the final products, examples 127–129 were prepared. ¹H NMR spectra and/or mass spectra were consistent with the structures in Table 5.

TABLE 5

| Example | R³ | R" | synthesis method |
|---|---|---|---|
| 127 | 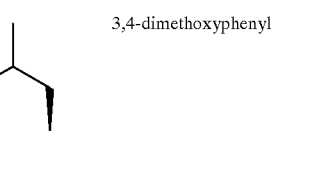 | 4-phenoxyphenyl | SPS |
| 128 |  | quinolin-2-yl | SPS |
| 129 | 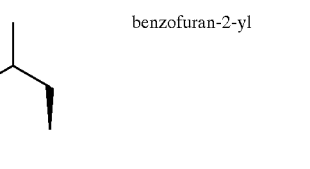 | 3,4-dimethoxyphenyl | SPS |

Example 130

Preparation of 4-(R,S)-Amino-N-[(benzo[b]thiophen-2-ylcarbonyl)-S-leucine]-tetrahydrothiophen-3-one (a) N-benzo[b]thiophene-2-ylcarbonyl-L-leucine methyl ester Benzo[b]thiophene-2-carbonyl chloride (4.9 g, 25 mmol) was added to a stirred solution of L-leucine methyl ester (4.5 g, 25 mmol) and diisopropylethylamine (9 ml, 51 mmol) in DCM (200 ml). After stirring for 2 hours at room temperature, the mixture was poured into water and washed with brine and dried (MgSO$_4$). Evaporation under reduced pressure afforded the title compound as a white solid, 7.6 g, 100% yield.

$^1$H NMR δ(CDCl$_3$, 250 MHz) 7.88-7.78 (m, 3 H), 7.44-7.38 (m, 2 H), 6.53 (d, 1 H, J=7.6 Hz), 4.91-4.82 (m, 1H), 3.78 (s, 3 H), 1.82-1.60 (m, 3 H), 1.00 (app t, 6 H, J=5.9 Hz).

(b) N-benzo[b]thiophene-2-ylcarbonyl-L-leucine

Lithium hydroxide (1.41 g, 59 mmol) was added in one portion to a stirred solution of N-benzo[b]thiophene-2-ylcarbonyl-L-leucine methyl ester (8.99 g, 29.4 mmol) in THF/H$_2$O (1/1, 300 ml). After stirring for 12 hours at room temperature, the mixture was poured into water and acidifed to pH 1 with cHCl and extracted with Et$_2$O (×2). Evaporation under reduced pressure afforded the title compound as a yellow solid, 6.1 g, 71% yield.

$^1$H NMR δ(d$_6$ DMSO, 250 MHz) 8.78 (d, 1 H, J=9.1 Hz), 8.12 (s, 1H), 7.92-7.83 (m 2 H), 7.36-7.30 (m, 2 H), 4.37-4.28 (m. 1H), 1.88-1.47 (m, 3 H), 0.82 (d, 3 H, J=6.0 Hz), 0.78 (d, 3 H, J=6.0 Hz).

(c) N-benzo[b]thiophene-2-ylcarbonyl-L-leucine-S-(methoxycarbonylmethyl)-L,D-cysteine ethyl ester Iso-Propyl chloroformate (5.9 ml, 1.0 M in toluene) was added to a stirred solution of N-benzo[b]thiophene-2-ylcarbonyl-L-leucine (1.65 g, 5.7 mmol) and triethylamine (1.6 ml. 11.8 mmol) in DCM (20 ml). After 1 hour at room temperature L-cysteine ethyl ester was added followed by triethylamine (1.6 ml, 11.8 mmol) and the mixture was allowed to stir for a further 6 hours. Methyl bromoacetate (0.6 ml, 6.3 mmol) was added and the mixture was left for a further 0.5 hours before being poured into water and extracted with EtOAc(×3). The combined organic layers were washed with brine, dried (MgSO$_4$) and evaporated under reduced pressure. Flash column chromatography (40% hexane-Et$_2$O) afforded the title compound as a white solid, 1.6 g, 70%.

$^1$H NMR δ(CDCl$_3$, 250 MHz) 7.84-7.77 (m, 3 H), 7.66 (d, 0.5 H. J=8.4 Hz), 7.52 (d, 0.5 H, J=8.4 Hz), 7.40-7.35 (m, 2 H), 7.24 (d, 0.5 H, J=8.4Hz), 7.16 (d, 0.5 H, J=8.4 Hz), 4.88-4.82 (m, 2 H), 4.23-4.15 (m, 2 H), 3.70 (s, 1.5 H), 3.69 (s, 1 H), 3.36-3.22 (m, 2 H), 3.15-3.08 (m, 2 H), 1.82-1.75 (m, 3 H), 1.28 (t, 1.5 H, J=4.5 Hz), 1.23 (t, 1.5 H, J=4.5 Hz), 0.98-0.95 (m, 6 H).

(d) 4-(R,S)-Amino-N-[(benzo[b]thiophene-2-ylcarbonyl)-S-leucine]-tetrahydrothiophene-3-one A solution of freshly prepared sodium methoxide (from 75 mg of sodium and 2 ml of methanol) was added to N-benzo[b]thiophene-2-ylcarbonyl-L-leucine-S-(carbomethoxymethyl)-L,D-cysteine ethyl ester (1.5 g, 3.2 mmol) in methanol (2 ml) at room temperature. After 1 hour Et$_2$O (80 ml) was added, the solution was cooled to 0° C. and the resulting white solid was filtered off. The solid was dissolved in 15 ml of glacial acetic acid, 10 ml of cHCl and 15 ml of H$_2$O. This mixture was stirred at reflux for 0.5 hours then cooled to room temperature and extracted with CHCl$_3$ (×5). The combined organic layers were washed with NAHCO$_3$, brine, dried (MgSO$_4$) and evaporated under reduced pressure. Flash column chromatography (40% hexane-Et$_2$O) afforded the title compound as a white solid, 120 mg, 10%.

$^1$H NMR δ(CDCl$_3$, 400 MHz) 7.88-7.78 (m, 3 H), 7.58 (d, 0.5 H, J=6.4 Hz), 7.54 (d, 0.5 H, J=6.4 Hz), 7.42-7.35 (m, 3 H), 4.85-4.80 (m, 1H), 4.43-4.34 (m, 1H), 3.34-3.23 (m, 3 H), 3.02-2.91 (m, 1 H), 1.76-1.74 (m, 3 H), 0.98-0.85 (in, 6 H).

MS calcd for (C$_{19}$H$_{22}$N$_2$O$_3$S+H)$^+$: 391. Found: 391.

Example 131

Preparation of 4-Amino-N-[(benzo[b]thiophen-2-ylcarbonyl)-S-leucine]-3.3-dimethoxytetrahydrofuran, diastereomer 1 a) 4-(R,S)-Amino-N-[(benzyloxycarbonyl)-S-leucine]-3,3-dimethoxytetrahydrofuran 4-(R,S)-Amino-3,3-dimethoxytetrahydrofuran (2.2 g, 15 mmol), N-benzyloxycarbonyl-L-leucine (3.98 g, 15 mmol), EDC (3.17 g, 16.5 mmol) and hydroxyaminobenztriazole (0.45 g, 3.3 mmol) were stirred togeather in a mixture of dichloromethane and tetrahydrofuran (1:1, 100 ml) at ambient temperature for 12 hr. The mixture was added to ethyl acetate (300 ml), washed with water (2×100 ml), dried ( MgSO$_4$) and evaporated to dryness. Chromatography of the resulting oil on silica gel (ethyl acetate/hexane 1:3 to 1:1 gradient) gave the title compound as an oil (5.27 g, 89%).

$^1$H NMR δ(CDCl$_3$) 7.34 (s, 5H), 6.55 (d, 1H), 5.11 (m, 3H), 4.34 (q, 1H, J=6.7Hz), 4.20 (m, 2H), 3.77 (s, 2H), 3.51 (m, 1H), 3.26 (d, 3H, J=2.3Hz), 3.2((d, 3H, J=4.7 Hz), 1.54 (m, 3H), 0.95 (s, 3H), 0.93 (s, 3H).

b) Separate diastereomers of 4-Amino-N-(S-leucine)-3,3-dimethoxytetrahydrofuran 4-(R,S)-Amino-N-(benzyloxycarbonyl)-S-leucine]-3,3-dimethoxytetrahydrofuran (5.27 g, 13.4 mmol) was subjected to hydrogenation at 50 psi in methanol containing 10% palladium on carbon. After 3.5 hr, the mixture was filtered through celite and the solvent was removed under reduced pressure. Chromatography of the resulting oil (3.5 g) on silica gel (CH$_2$Cl$_2$ containing MeOH, 0–4% gradient) separated the title compound into the two pure single diastereomers: diastereomer 1 (faster running) (0.63 g). $^1$H NMR δ(CDCl$_3$) 7.76 (d, 1H, J=7.3Hz), 4.36 (dd, 1H, J=6.3, 7.2 Hz), 4.21 (dd, 1H, J=6.4 , 9.0 Hz), 3.80 (s, 2H), 3.57 (dd, 1H, J=5.3, 9.1 Hz), 3.41 (dd, 1H, J=3.8, 10.1Hz), 3.30 (s, 3H), 3.24 (s, 3H), 1.73 (m, 2H), 1.35 (m, 1H), 0.96 (d,3H, J=6.7 Hz), 0.94 (d, 3H, J=6.6 Hz)

diastereomer 2 (slower running) (0.91 g) $^1$H NMR δ(CDCl$_3$) 7.77 (d, 1H, J=7.1 Hz), 4.36 (dd, 1H, J=6.4, 12.9 Hz), 4.21 (dd, 1H, J=6.5, 9.1 Hz), 3.80 (s, 2H), 3.55 (dd, 1H, J=5.3, 9.0), 3.38 (dd, 1H, j=4.0, 10.0), 3.30 (s, 3H), 3.25 (s, 3H), 1.72 (m, 2H), 1.38 (m, 1H), 0.96 (d, 3H,J=6.7 Hz), 0.94 (d, 3H, J=6.8 Hz).

c) 4-Amino-N-[(benzo[b]thiophen-2-ylcarbonyl)-S-leucine]-3,3-dimethoxytetrahydrofuran, diastereomer 1

Saturated sodium bicarbonate solution (5 ml) was added to a solution of 4-amino-N-(S-leucine)-3,3-dimethoxytetrahydrofuran, diastereomer 1 (0.13 g, 0.5 mmol) in 1.4-dioxane (5 ml) followed by benzo[b]thiophen-2-ylcarbonyl chloride (0.39 g, 2 mmol). After 45 minutes, the mixture was added to ethyl acetate, washed with water, sodium bicarbonate solution and water. The organic solution was then dried ( MgSO$_4$) and evaporated to give a white solid (0.47 g). Chromatography on silica gel (CH$_2$Cl$_2$ containing MeOH 0–5% gradient ) gave the title compound (0.18 g, 89%) as a white solid, $^1$H NMR δ(CDCl$_3$) 7.88 (s, 1H), 7.74 (m, 3H), 7.34 (m, 2H), 7.18 (d, 1H, J=7.1 Hz), 4.82 (m, 1H), 4.38 (dd, 1H, J=6.4, 12.3 Hz), 4.21 (dd, 1H, J=6.5, 9.2 Hz), 3.78 (ABq, 2H, J=3.8, 9.8 Hz), 3.62 (dd, 1H, J=5.2, 9.1 Hz), 1.78 (m, 3H), 0.99 (s, 3H), 0.96 (s, 3H).

Examples 132–142

By analgous procedures to those described in example 131, using the appropriate diastereomer of 4-amino-N-(S-leucine)-3,3-dimethoxytetrahydrofuran and the carboxylic acid halide reagents consistent with the final products, the compounds of Table 6 were also prepared. $^1$H NMR and mass spectra were consistent with the structures in Table 6.

TABLE 6

| Example | R³ | R" | Rᵃ | Rᵃ' | diastereomer |
|---|---|---|---|---|---|
| 132 | isobutyl | benzo[b]thiophen-2-yl | Me | Me | 2 |
| 133 | isobutyl | indol-5-yl | " | " | 1 |
| 134 | isobutyl | " | " | " | 2 |
| 135 | isobutyl | quinolin-2-yl | " | " | 1 |
| 136 | isobutyl | " | " | " | 2 |
| 137 | isobutyl | 3-bromophenyl | " | " | 1 |
| 138 | isobutyl | " | " | " | 2 |
| 139 | isobutyl | 4-phenoxyphenyl | " | " | 1 |
| 140 | isobutyl | " | " | " | 2 |

TABLE 6-continued

| Example | R³ | R" | Rᵃ | Rᵃ' | diastereomer |
|---|---|---|---|---|---|
| 141 | isobutyl | indole-6-yl | " | " | 2 |
| 142 | isobutyl | benzimidazol-5-yl | | | 1 |

Example 143

Preparation of 4-Amino-N-[(benzo[b]thiophen-2-ylcarbonyl)-S-leucine]-3,3-dimethoxytetrahydropyran diastereomer 1 a) 4-(R,S)-Amino-N-(benzyloxycarbonyl)-S-leucine]-3,3-dimethoxytetrahydropyran 4-(R,S)-amino-N-[(benzyloxycarbonyl)-S-leucine] tetrahydropyran-3-one (example 67c, 3.1 g, 8.6 mmol) was heated at reflux for 12 hr with trimethylorthoformate (2.8 ml) and p-toluenesulphonic acid (0.080 g) in methanol (50 ml). After removing the solvent under reduced pressure, the resulting oil was chromatographed on silica gel (ethyl acetate/hexane gradient) to give the title compound as a white solid (2.89 g, 80%)

$^1$H NMR δ(CDCl$_3$) 7.29 (s, 5H), 6.99 (m, 1H), 6.15 (m, 1H), 5.07 (s, 2H), 4.28 (m, 1H), 4.18(m, 1H), 3.52 (m 4H), 3.19 (s, 3H), 3.14 (s, 3H), 1.85 (m, 1H), 1.63 (m, 4H), 0.93 (s, 6H).

b) Separate diastereomers of 4-Amino-N-(S-leucine)-3,3-dimethoxytetrahydropyran 4-(R,S)-Amino-N-[(benzyloxycarbonyl)-S-leucine]-3,3-dimethoxytetrahydropyran was hydrogenated as in example 131b to give, after chromatography, the pure single diastereomers of the title compound:

diastereomer 1: $^1$H NMR δ(CDCl$_3$) 7.75 (d, 1H, J=8.1 Hz), 4.17 (m, 1H), 3.58 (m, 3H), 3.41 (dd, 1H, J=3.5, 9.7 Hz), 3.28 (s, 3H), 3.24 (s, 3H), 1.92 (m, 1H), 1.71 (m, 4H), 1.30 (m, 1H). 0.97 (d, 3H, J=6.4 Hz), 0.94 (d, 3H, J=6.3 Hz).

diastereomer 2: $^1$H NMR δ(CDCl$_3$) 7.8 (s, 1H), 4.16 (m, 1H), 3.59 (m, 3H), 3.49 (m, 1H), 3.28 (s, 3H), 3.24 (s, 3H), 1.92 (m, 1H), 1.72 (m, 4H), 1.41 (m, 1H), 0.97 (d, 3H, J=6.1 Hz), 0.95 (d, 3H J=6.0 Hz).

c) 4-Amino-N-[(benzo[b]thiophen-2-ylcarbonyl)-S-leucine]-3,3-dimethoxytetrahydropyran, diastereomer 1

4-Amino-N-(S-leucine)-3,3-dimethoxytetrahydropyran diastereomer 1 was reacted with benzo[b]thiophen-2-ylcarbonyl chloride, as in example 131c, to give the title compound.

$^1$H NMR δ(CDCl$_3$) 7.98 (d, 1H, J=8.3 Hz), 7.93 (s, 1H), 7.78 (d, 1H,J=7.7 Hz), 7.71 (d, 1H, J=8.3 Hz), 7.33 (m, 3H), 4.83 (m, 1H), 4.19 (m, 1H), 3.69 (m, 1H), 3.57 (m, 2H), 3.40 (d, 1H, J=13 Hz). 3.23 (s, 3H), 3.13 (s, 3H), 1.85 (m, 5H), 0.98 (d, 3H, J=4.8 Hz), 0.96 (d, 3H, J=5.2 Hz).

Example 144
Preparation of 4-Amino-N-[(benzo[b]thiophen-2-ylcarbonyl)-S-leucine]-3,3-dimethoxytetrahydropyran diastereomer 2

Using diastereomer 2 of 4-amino-N-(S-leucine)-3,3-dimethoxytetrahydropyran in the procedure of example 143c, the title compound was prepared.

The above specification and Examples fully disclose how to make and use the compounds of the present invention However, the present invention is not limited to the particular embodiments described hereinabove, but includes all modifications thereof within the scope of the following claims. The various references to journals, patents and other publications which are cited herein comprise the state of the art and are incorporated herein by reference as though fully set forth.

What is claimed is:

1. A compound according to formula (I):

(I)

wherein:
$R^1$ is R", R"C(O), R"C(S), R"SO$_2$, R"OC(O), R"R'NC(O), or R"OC(O)NR'CH(R$^6$)C(O);
$R^2$ is H, $C_{1-6}$alkyl, $C_{2-6}$alkenyl, Ar-$C_{0-6}$alkyl, or Het-$C_{0-6}$alkyl;
$R^3$ is H, $C_{1-6}$alkyl, $C_{2-6}$alkenyl, $C_{2-6}$alkynyl, $C_{3-6}$cycloalkyl-$C_{0-6}$alkyl, Ar-$C_{0-6}$alkyl, or Het-$C_{0-6}$alkyl;
$R^4$ is H, $C_{1-6}$alkyl, $C_{2-6}$alkenyl, Ar-$C_{0-6}$alkyl, or Het-$C_{0-6}$alkyl;
each $R^5$ independently is H, $C_{1-6}$alkyl, $C_{2-6}$alkenyl, Ar-$C_{0-6}$alkyl, or Het-$C_{0-6}$alkyl;
$R^6$ is H, $C_{1-6}$alkyl, $C_{2-6}$alkenyl, $C_{3-6}$cycloalkyl-$C_{0-6}$alkyl, Ar-$C_{0-6}$alkyl, Het-$C_{0-6}$alkyl;
R' is H, $C_{1-6}$alkyl, $C_{2-6}$alkenyl, Ar-$C_{0-6}$alkyl, or Het-$C_{0-6}$alkyl;
R" is in which $B_2$ is OH, CN, OCF$_3$, OC$_{1-6}$alkyl, OAr, SO$_2$C$_{1-6}$alkyl, C$_{1-6}$alkyl or halo;
X is O or S;
n is 1, 2, or 3;
or a pharmaceutically acceptable salt thereof.

2. A compound according to claim 1 wherein $R^2$ and $R^4$ are each H.

3. A compound according to claim 1 wherein $R^3$ is $C_{1-6}$alkyl or $C_{2-6}$alkenyl.

4. A compound according to claim 3 wherein $R^3$ is i-butyl.

5. A compound according to claim 1 wherein $R^1$ is R"OC(O), R"SO$_2$ or R"C(O).

6. A compound according to claim 1 wherein n is 1 or 2.

7. A compound according to claim 6 wherein n is 1.

8. A compound according to claim 1 wherein X is O.

9. A compound according to claim 1 wherein each $R^5$ is H.

10. A compound according to claim 1 of the formula (IIa):

(IIa)

11. A compound according to claim 1 of the formula (IIb):

(IIb)

12. A compound according to claim 1 of the formula (IIc):

(IIc)

13. A compound which is:
4-(R,S)-Amino-N-[(3,4-methylenedioxybenzoyl)-S-leucine]-tetrahydrofuran-3-one;
4-(R,S)-Amino-N-[(benzyloxycarbonyl)-S-leucine]-tetrahydrofuran-3-one;
4-(R,S)-Amino-N-[(3,4-dichlorobenzoyl)-S-leucine]-tetrahydrofuran-3-one;
4-(R,S)-Amino-N-[(2-quinolinecarbonyl)-S-leucine]-tetrahydrofuran-3-one;
4-(R,S)-Amino-N-[(8-quinolinecarbonyl)-S-leucine]-tetrahydrofuran-3-one;

4-(R,S)-Amino-N-[(benzyloxycarbonyl)-S-leucine]-2,2-dibenzyl-tetrahydrofuran-3-one;

4-(R,S)-Amino-N-[(benzo[b]thiophen-2-ylcarbonyl)-S-leucine]-tetrahydrofuran-3-one;

4-(R,S)-Amino-N-[(3,4-dimethoxybenzoyl)-S-leucine]-tetrahydrofuran-3-one;

4-(R,S)-Amino-N-[(indole-6-ylcarbonyl)-S-leucine]-tetrahydrofuran-3-one;

4-(R,S)-Amino-N-[(benzofuran-2-ylcarbonyl)-S-leucine]-tetrahydrofuran-3-one;

4-(R,S)-Amino-N-[(5-aminobenzo[b]thiophen-2-ylcarbonyl)-S-leucine]-tetrahydrofuran-3-one;

4-(R,S)-Amino-N-[(5-chlorobenzofuran-2-ylcarbonyl)-S-leucine]-tetrahydrofuran-3-one;

4-(R,S)-Amino-N-[(5-methoxybenzofuran-2-ylcarbonyl)-S-leucine]-tetrahydrofuran-3-one;

4-(R,S)-Amino-N-[(3-bromobenzoyl)-S-leucine]-tetrahydrofuran-3-one;

4-(R,S)-Amino-N-[(4-bromobenzoyl)-S-leucine]-tetrahydrofuran-3-one;

4-(R,S)-Amino-N-[(5-chlorobenzo[b]thiophen-2-ylcarbonyl)-S-leucine]-tetrahydrofuran-3-one;

4-(R,S)-Amino-N-[(4-fluorobenzo[b]thiophen-2-ylcarbonyl)-S-leucine]-tetrahydrofuran-3-one;

4-(R,S)-Amino-N-[(4-phenoxybenzoyl)-S-leucine]-tetrahydrofuran-3-one;

4-(R,S)-Amino-N-[(4-phenylbenzoyl)-S-leucine]-tetrahydrofuran-3-one;

4-(R,S)-Amino-N-[(6-trifluoromethylbenzo[b]thiophen-2-ylcarbonyl)-S-leucine]-tetrahydrofuran-3-one;

4-(R,S)-Amino-N-[(4-ethylbenzoyl)-S-leucine]-tetrahydrofuran-3-one;

4-(R,S)-Amino-N-[(4-(tert-butyl)benzoyl)-S-leucine]-tetrahydrofuran-3-one;

4-(R,S)-Amino-N-[(5-methoxybenzo[b]thiophen-2-ylcarbonyl)-S-leucine]-tetrahydrofuran-3-one;

4-(R,S)-Amino-N-[(4-nitrobenzo[b]thiophen-2-ylcarbonyl)-S-leucine]-tetrahydrofuran-3-one;

4-(R,S)-Amino-N-[(6-bromobenzo[b]thiophen-2-ylcarbonyl)-S-leucine]-tetrahydrofuran-3-one;

4-(R,S)-Amino-N-[(5-bromobenzo[b]thiophen-2-ylcarbonyl)-S-leucine]-tetrahydrofuran-3-one;

4-(R,S)-Amino-N-[(6-methoxybenzo[b ]thiophen-2-ylcarbonyl)-S-leucine]-tetrahydrofuran-3-one;

4-S-Amino-N-[(benzo(b)thiophen-2-ylcarbonyl)-S-leucine]-tetrahydrofuran-3-one;

4-R-Amino-N-[(benzo(b)thiophen-2-ylcarbonyl)-S-leucine]-tetrahydrofuran-3-one;

4-S-Amino-N-[(2-napthoyl)-S-leucine]-tetrahydrofuran-3-one;

4-R-Amino-N-[(2-napthoyl)-S-leucine]-tetrahydrofuran-3-one;

4-S-Amino-N-[(quinoline-2-carbonyl)-S-leucine]-tetrahydrofuran-3-one;

4-R-Amino-N-[(quinoline-2-carbonyl)-S-leucine]-tetrahydrofuran-3-one;

4-S-Amino-N-[(5-methoxybenzofuran-2-ylcarbonyl)-S-leucine]-tetrahydrofuran-3-one;

4-S-Amino-N-[((4-pyrid-3-yl)benzoyl)-S-leucine]-tetrahydrofuran-3-one;

4-S-Amino-N-[((4-pyrid-2-yl)benzoyl)-S-leucine]-tetrahydrofuran-3-one;

4-S-Amino-N-[(benzyloxycarbonyl)-S-leucine]-tetrahydrofuran-3-one;

4-S-Amino-N-[(3,4-dimethoxybenzoyl)-S-leucine]-tetrahydrofuran-3-one;

4-S-Amino-N-[(benzofuran-2-ylcarbonyl)-S-leucine]-tetrahydrofuran-3-one;

4-S-Amino-N-[(4-[6-methylpyrid-3-yl]benzoyl)-S-leucine]-tetrahydrofuran-3-one;

4-S-Amino-N-[(5-chlorobenzo[b]thiophen-2-ylcarbonyl)-S-leucine]-tetrahydrofuran-3-one;

4-S-Amino-N-[((4-pyrid-4-yl)benzoyl)-S-leucine]-tetrahydrofuran-3-one;

4-S-Amino-N-[(2-chlorobenzoyl)-S-leucine]-tetrahydrofuran-3-one;

4-S-Amino-N-[(4-bromobenzoyl)-S-leucine]-tetrahydrofuran-3-one;

4-S-Amino-N-[(4-chlorobenzo[b]thiophen-2-ylcarbonyl)-S-leucine]-tetrahydrofuran-3-one;

4-S-Amino-N-[(4-benzylpiperidin-1-ylcarbonyl)-S-leucine]-tetrahydrofuran-3-one;

4-S-Amino-N-[(3,4-dichlorobenzoyl)-S-leucine]-tetrahydrofuran-3-one;

4-S-Amino-N-[(3-chlorobenzoyl )-S-leucine]-tetrahydrofuran-3-one;

4-(R,S)-Amino-N-[(3,4-dimethoxybenzoyl)-S-leucine]-tetrahydropyran-3-one;

4-(R,S)-Amino-N-[(4-phenoxybenzoyl)-S-leucine]-tetrahydropyran-3-one;

4-(R,S)-Amino-N-[(quinolin-2-ylcarbonyl)-S-leucine]-tetrahydropyran-3-one;

4-(R,S)-Amino-N-[(benzyloxycarbonyl)-S-leucine]-tetrahydropyran-3-one;

4-(R,S)-Amino-N-[(benzo[b]thiophen-2-ylcarbonyl)-S-leucine]-tetrahydropyran-3-one; or 4-(R,S)-Amino-N-[(benzo[b]thiophen-2-ylcarbonyl)-S-leucine]-tetrahydrothiophen-3-one;

or a pharmaceutically acceptable salt thereof.

14. A pharmaceutical composition comprising a compound according to any one of claims 1–13 and a pharmaceutically acceptable salt thereof.

15. A method of inhibiting a cysteine protease which comprises administering to a patient in need thereof an effective amount of a compound according to claim 1.

16. A method according to claim 15 wherein the cysteine protease is cathepsin K.

17. A method of inhibiting bone loss which comprises administering to a patient in need thereof an effective amount of a compound according to claim 1.

18. A method of treating osteoporosis which comprises administering to a patient in need thereof an effective amount of a compound according to claim 1.

19. A process for preparing a compound of the formula (I) as defined in claim 1, which process comprises:

(i) reacting a compound of the formula (III):

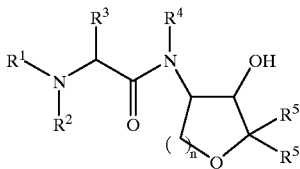
(III)

wherein $R^1$, $R^2$, $R^3$, $R^4$, $R^5$ and n are as defined in formula (I) of claim 1, with any reactive functional groups protected, with an oxidizing agent; or (ii) decarboxylating a compound of the formula (IV):

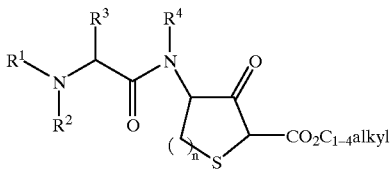
(IV)

wherein $R^1$, $R^2$, $R^3$, $R^4$, $R^5$ and n are as defined in formula (I) of claim 1, with any reactive functional groups protected; or (iii) reacting a compound of the formula (V):

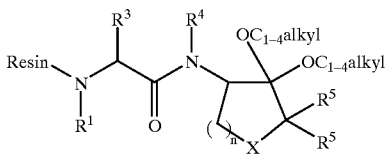
(V)

wherein $R^1$, $R^3$, $R^4$, $R^5$ and n are as defined in formula (I) of claim 1, with any reactive functional groups protected, with an acid;

and thereafter removing any protecting groups and optionally forming a pharmaceutically acceptable salt.

20. A compound according to formula (IV):

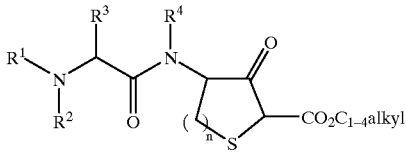
(IV)

wherein:
$R^1$ is R", R"C(O), R"C(S), R"SO$_2$, R"OC(O), R"R'NC(O), or R"OC(O)NR'CH(R$^6$)C(O);
$R^2$ is H, C$_{1-6}$alkyl, C$_{2-6}$alkenyl, Ar-C$_{0-6}$alkyl, or Het-C$_{0-6}$alkyl;
$R^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;
$R^4$ is H, C$_{1-6}$alkyl, C$_{2-6}$alkenyl, Ar-C$_{0-6}$alkyl, or Het-C$_{0-6}$alkyl;
each $R^5$ independently is H, C$_{1-6}$alkyl, C$_{2-6}$alkenyl, Ar-C$_{0-6}$alkyl, or Het-C$_{0-6}$alkyl;
$R^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;
R' is H, C$_{1-6}$alkyl, C$_{2-6}$alkenyl, Ar-C$_{0-6}$alkyl, or Het-C$_{0-6}$alkyl;
R" is C$_{1-6}$alkyl, Ar-C$_{0-6}$alkyl, Het-C$_{0-6}$alkyl, Ar-C$_{2-6}$alkenyl or Het-C$_{2-6}$alkenyl; and
n is 1, 2 or 3;
or a pharmaceutically acceptable salt thereof.

21. A compound according to formula (V):

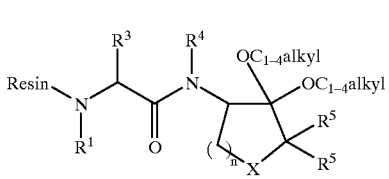
(V)

wherein:
$R^1$ is R", R"C(O), R"C(S), R"SO$_2$, R"OC(O), R"R'NC(O), or R"OC(O)NR'CH(R$^6$)C(O);
$R^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;
$R^4$ is H, C$_{1-6}$alkyl, C$_{2-6}$alkenyl, Ar-C$_{0-6}$alkyl, or Het-C$_{0-6}$alkyl;
each $R^5$ independently is H, C$_{1-6}$alkyl, C$_{2-6}$alkenyl, Ar-C$_{0-6}$alkyl, or Het-C$_{0-6}$alkyl;
$R^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;
R' is H, C$_{1-6}$alkyl, C$_{2-6}$alkenyl, Ar-C$_{0-6}$alkyl, or Het-C$_{0-6}$alkyl;
R" is C$_{1-6}$alkyl, Ar-C$_{0-6}$alkyl, Het-C$_{0-6}$alkyl, Ar-C$_{2-6}$alkenyl or Het-C$_{2-6}$alkenyl;
X is O or S; and
n is 1, 2 or 3;
or a pharmaceutically acceptable salt thereof.

22. A compound according to formula (VI):

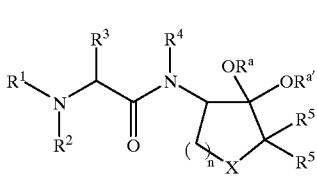
(VI)

wherein:
$R^1$ is R", R"C(O), R"C(S), R"SO$_2$, R"OC(O), R"R'NC(O), or R"OC(O)NR'CH(R$^6$)C(O);
$R^2$ is H, C$_{1-6}$alkyl, C$_{2-6}$alkenyl, Ar-C$_{0-6}$alkyl, or Het-C$_{0-6}$alkyl;
$R^3$ is H, C$_{1-6}$alkyl, C$_{2-6}$alkenyl, C$_{2-6}$alkynyl, C$_{3-6}$cycloalkyl-C$_{0-6}$alkyl, Ar-C$_{0-6}$alkyl, or Het-C$_{0-6}$alkyl;
$R^4$ is H, C$_{1-6}$alkyl, C$_{2-6}$alkenyl, Ar-C$_{0-6}$alkyl, or Het-C$_{0-6}$alkyl;
each $R^5$ independently is H, C$_{1-6}$alkyl, C$_{2-6}$alkenyl, Ar-C$_{0-6}$alkyl, or Het-C$_{0-6}$alkyl;
$R^6$ is H, C$_{1-6}$alkyl, C$_{2-6}$alkenyl, C$_{3-6}$cycloalkyl-C$_{0-6}$alkyl, Ar-C$_{0-6}$alkyl, Het-C$_{0-6}$alkyl;
R' is H, C$_{1-6}$alkyl, C$_{2-6}$alkenyl, Ar-C$_{0-6}$alkyl, or Het-C$_{0-6}$alkyl;

R" is $C_{1-6}$alkyl, Ar-$C_{0-6}$alkyl, Het-$C_{0-6}$alkyl, Ar-$C_{2-6}$alkenyl; or Het-$C_{2-6}$alkenyl;

X is O or S;

n is 1, 2 or 3; and $R^a$ and $R^{a'}$ independently are H or $C_{1-2}$alkyl, with the proviso that when one of $R^a$ and $R^{a'}$ is H, the other is $C_{1-2}$alkyl; or together are $(CH_2)_{2-3}$ forming a 5- or 6-membered ring;

or a pharmaceutically acceptable salt thereof.

* * * * *